(12) United States Patent
De et al.

(10) Patent No.: US 11,136,542 B2
(45) Date of Patent: Oct. 5, 2021

(54) PERFUSION BIOREACTOR AND METHOD FOR USING SAME TO PERFORM A CONTINUOUS CELL CULTURE

(71) Applicant: Corning Incorporated, Corning, NY (US)

(72) Inventors: Sumitava De, Painted Post, NY (US); Yulong Hong, Painted Post, NY (US); Nikolaos Pantelis Kladias, Horseheads, NY (US); Shawn Michael O'Malley, Horseheads, NY (US); Aravind Raghavan Rammohan, Big Flats, NY (US); Po Ki Yuen, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 190 days.

(21) Appl. No.: 16/077,573

(22) PCT Filed: Feb. 13, 2017

(86) PCT No.: PCT/US2017/017624
§ 371 (c)(1),
(2) Date: Aug. 13, 2018

(87) PCT Pub. No.: WO2017/146928
PCT Pub. Date: Aug. 31, 2017

(65) Prior Publication Data
US 2019/0048305 A1  Feb. 14, 2019

Related U.S. Application Data

(60) Provisional application No. 62/366,372, filed on Jul. 25, 2016, provisional application No. 62/298,691, filed on Feb. 23, 2016.

(51) Int. Cl.
*C12N 1/00* (2006.01)
*C12M 1/04* (2006.01)
(Continued)

(52) U.S. Cl.
CPC ............ *C12M 29/10* (2013.01); *C12M 23/20* (2013.01); *C12M 23/24* (2013.01); *C12M 23/26* (2013.01);
(Continued)

(58) Field of Classification Search
CPC ...... C12M 29/10; C12M 29/06; C12M 29/20; C12M 29/04; C12M 27/02; C12M 23/20;
(Continued)

(56) References Cited

U.S. PATENT DOCUMENTS 5,602,028 A * 2/1997 Minchinton ........... C12M 25/02
210/615
5,658,797 A  8/1997 Bader
(Continued)

FOREIGN PATENT DOCUMENTS

CN   202415546 U   9/2012
CN   102978113 A   3/2013
(Continued)

OTHER PUBLICATIONS

Machine Translation of JP 05-095778 A (Year: 2020).*
(Continued)

*Primary Examiner* — Michael L Hobbs
(74) *Attorney, Agent, or Firm* — F. Brock Riggs

(57) ABSTRACT

A perfusion bioreactor and a method for using the perfusion bioreactor for performing a continuous cell culture are disclosed. The perfusion bioreactor includes an outer vessel having a housing with a gas permeable membrane, an opening and a cavity; an inner vessel within the cavity; and a lid to cover the opening. A porous membrane within the
(Continued)

cavity divides the cavity into inner and outer compartments. A fresh media port extends through the outer vessel or the at least one lid to receive a fresh media tube that has an end located in the inner compartment. A spent media port extends through the outer vessel or the at least one lid to receive a spent media tube that has an end located in the outer compartment. A mixer is within the inner compartment, and the porous membrane is attached to an opening within the inner vessel.

18 Claims, 19 Drawing Sheets

(51) Int. Cl.
  *C12M 1/00* (2006.01)
  *C12M 1/06* (2006.01)
  *C12M 1/12* (2006.01)
(52) U.S. Cl.
  CPC ............ *C12M 23/34* (2013.01); *C12M 27/02* (2013.01); *C12M 29/04* (2013.01); *C12M 29/06* (2013.01); *C12M 29/20* (2013.01); *C12M 37/02* (2013.01)
(58) Field of Classification Search
  CPC ...... C12M 23/34; C12M 23/26; C12M 23/24; C12M 37/02
  See application file for complete search history.

(56) References Cited

U.S. PATENT DOCUMENTS

| | | | |
|---|---|---|---|
| 6,297,046 | B1 | 10/2001 | Smith et al. |
| 6,864,084 | B2 | 3/2005 | Schob |
| 9,109,193 | B2 | 8/2015 | Galliher et al. |
| 9,364,776 | B2 | 6/2016 | Niazi |
| 2004/0241790 | A1* | 12/2004 | Eriksen ............... A23J 1/005 435/41 |
| 2011/0263021 | A1* | 10/2011 | Stobbe ............... C12M 23/42 435/398 |
| 2014/0370588 | A1 | 12/2014 | Castillo Gonzalez et al. |
| 2015/0210971 | A1 | 7/2015 | Baskar et al. |

FOREIGN PATENT DOCUMENTS

| | | | | |
|---|---|---|---|---|
| EP | 1186653 | A2 | 3/2002 | |
| JP | 62-122580 | A | 6/1987 | |
| JP | 01-206989 | A | 8/1989 | |
| JP | 02-057174 | A | 2/1990 | |
| JP | 02-076571 | A | 3/1990 | |
| JP | 05095778 | A * | 4/1993 | ............ C12M 21/18 |
| JP | 2002-508954 | A | 3/2002 | |
| JP | 2008-237122 | A | 10/2008 | |
| JP | 2011-177046 | A | 9/2011 | |
| JP | 2014-091079 | A | 5/2014 | |
| JP | 2015-500033 | A | 1/2015 | |
| WO | 1992005242 | A1 | 4/1992 | |
| WO | 1994017178 | A1 | 8/1994 | |
| WO | WO-9417178 | A1 * | 8/1994 | ............ C12M 25/18 |
| WO | 2007/023711 | A1 | 3/2007 | |
| WO | 2011/005773 | A2 | 1/2011 | |
| WO | 2013086371 | A1 | 6/2013 | |
| WO | 2013/126560 | A2 | 8/2013 | |
| WO | 2014/156998 | A1 | 10/2014 | |
| WO | 2015/040501 | A1 | 3/2015 | |

OTHER PUBLICATIONS

"Ambr® 15 Cell Culture-System Overview; The Leading Microbioreactor System for Cell Line Development and Process Optimisation"; Sartorius Stedim Biotech; 9 Pages; Downloaded May 12, 2016.
"Cell Culture Equipment (Hardware & Devices)"; Lab Times; Jan. 2006; pp. 52-58.
2nd International Symposium on Continuous Manufacturing of Pharmaceuticals; CMAC; Sep. 26-27, 2016; 4 Pages; https://iscmp.mit.edu/white-papers/introductory-white-paper.
Corning, Transwell, Snapwell™, Netwell®, and Falcon® Permeable Supports; 7 Pages; Downloaded Jun. 23, 2016.
International Search Report and Written Opinion of the International Searching Authority; PCT/US2017/017624; dated May 10, 2017; 12 Pages; European Patent Office.
Langer et al; "Continuous Bioprocessing and Perfusion: Wider Adoption Coming as Bioprocessing Matures"; Bioprocessing Journal; Spring 2014; pp. 50-55.
Japanese Patent Application No. 2018-563376 Notice of Reasons for Refusal dated Sep. 30, 2020; 12 Pages; Japanese Patent Office.

* cited by examiner

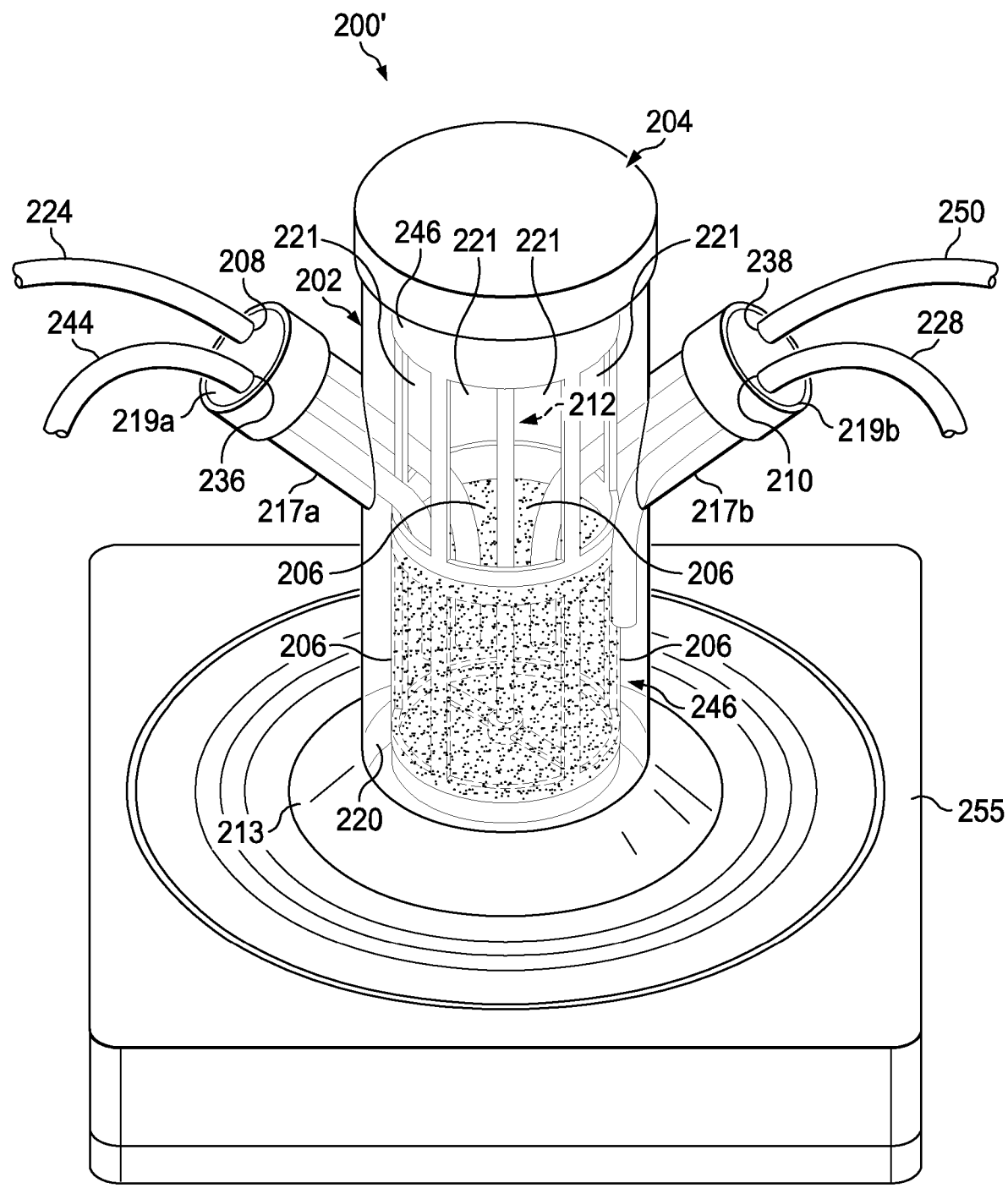
FIG. 5D1

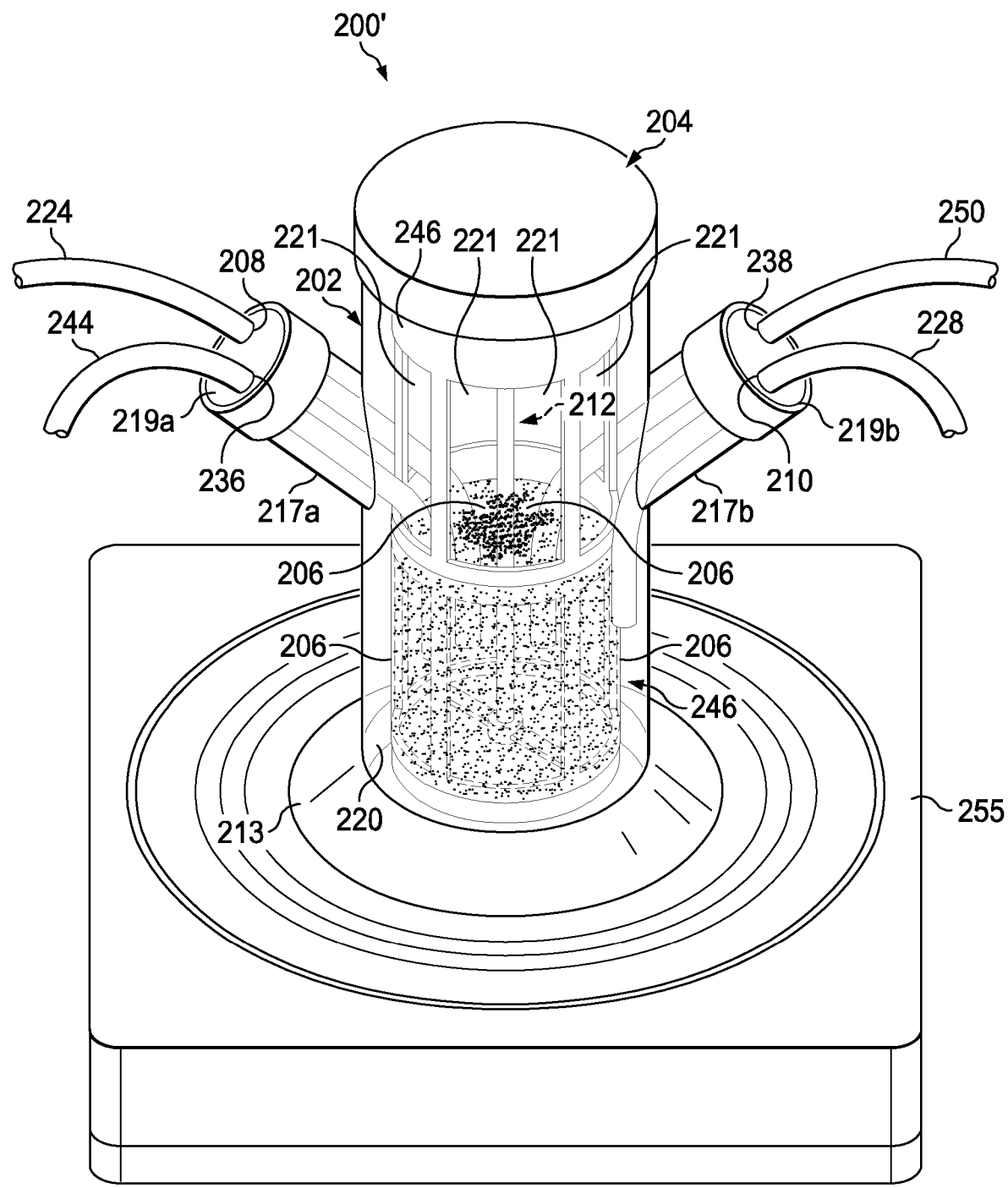
FIG. 5D2

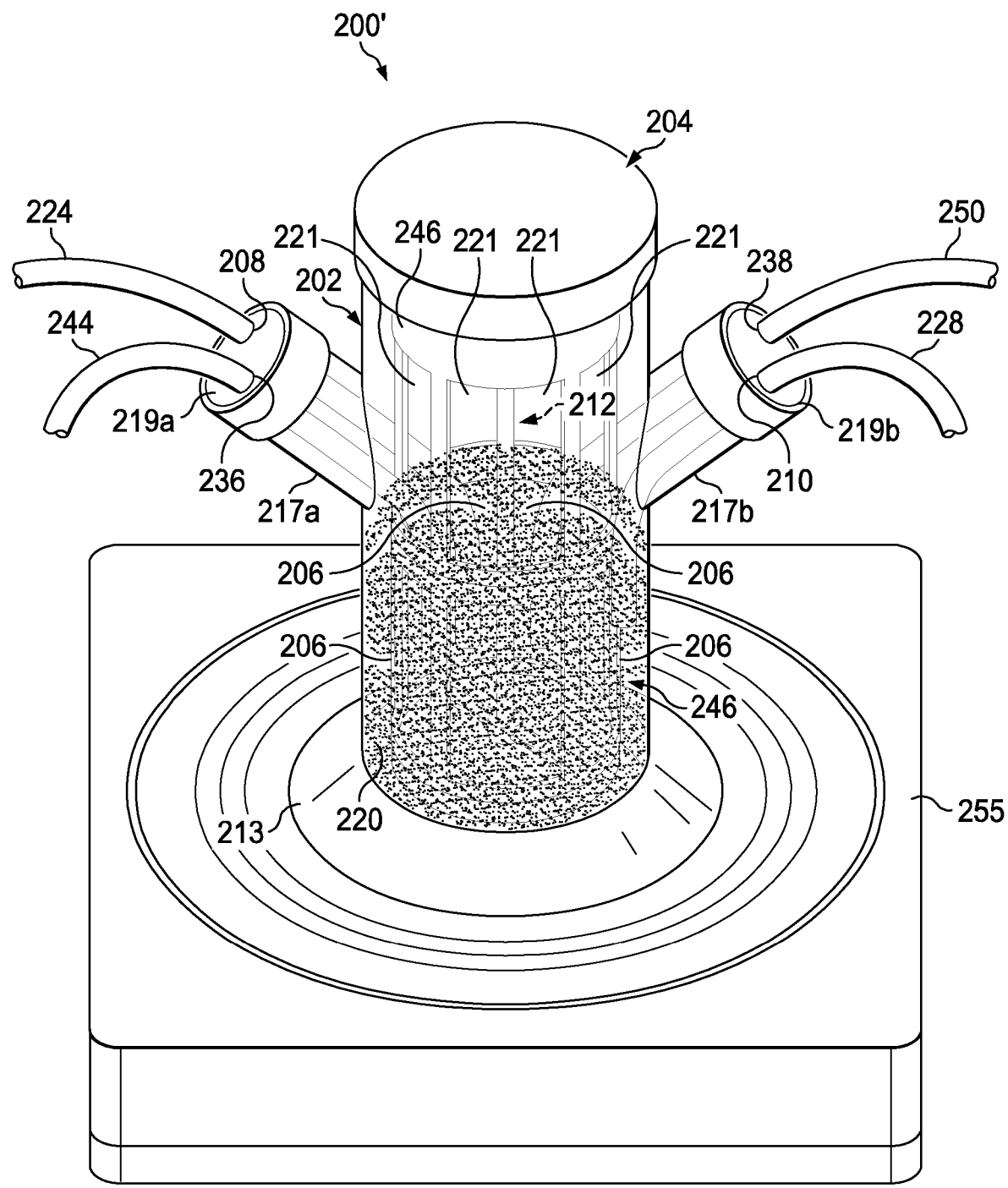
FIG. 5D3

FIG. 5F2

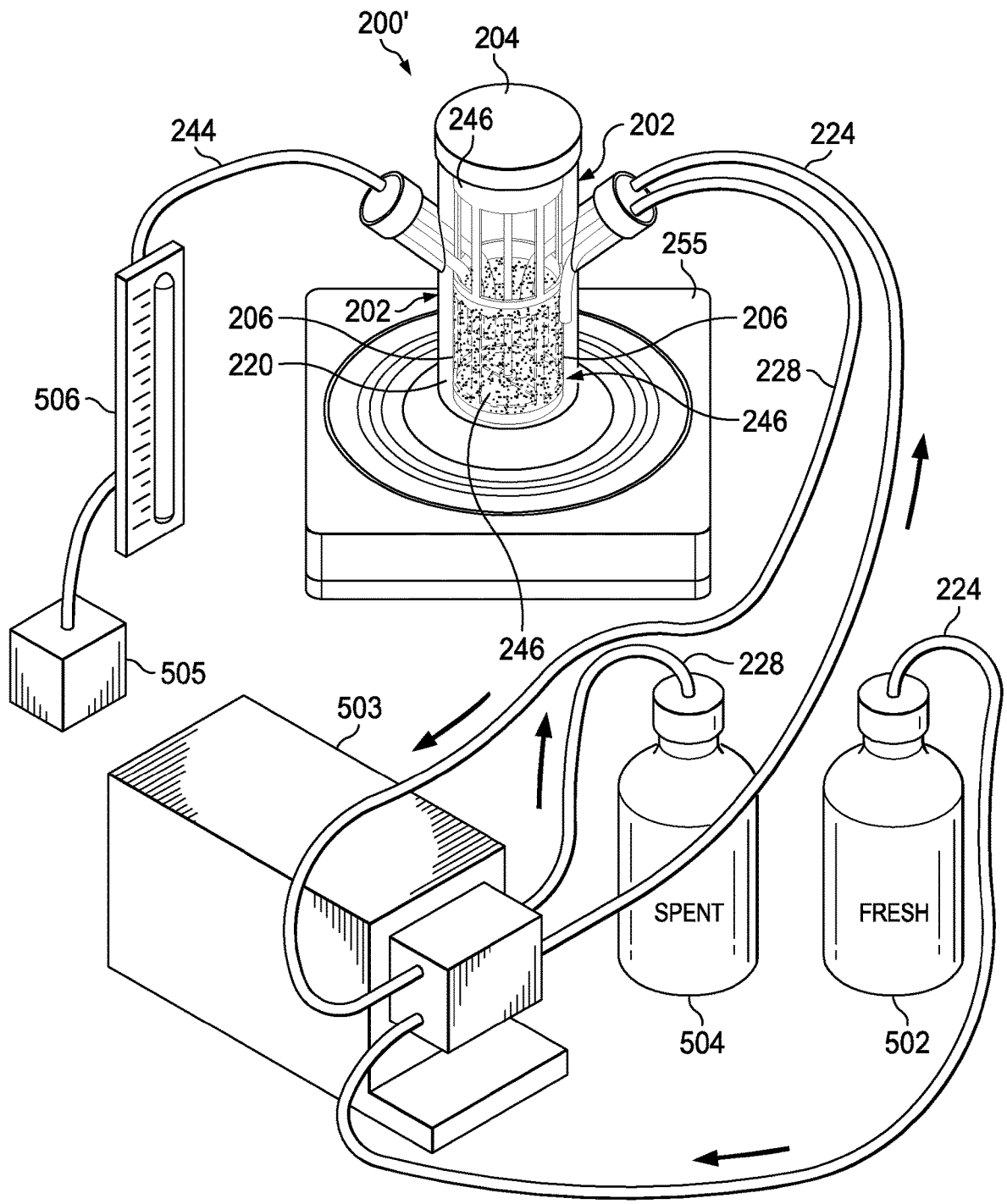
FIG. 5F1

PERFUSION BIOREACTOR AND METHOD FOR USING SAME TO PERFORM A CONTINUOUS CELL CULTURE

CROSS-REFERENCE TO RELATED APPLICATIONS

This application claims the benefit of priority under 35 U.S.C. § 371 of International Patent Application Serial No. PCT/US17/17624, filed on Feb. 13, 2017, which in turn, claims the benefit of priority of U.S. Provisional Patent Application Ser. No. 62/366,372 filed on Jul. 25, 2016, and U.S. Provisional Patent Application Ser. No. 62/298,691 filed on Feb. 23, 2016, the contents of each of which are relied upon and incorporated herein by reference in their entireties.

TECHNICAL FIELD

The present disclosure generally relates to the bioprocess field and, in particular, to a perfusion bioreactor and a method for using the perfusion bioreactor for performing a continuous cell culture.

BACKGROUND

Bioprocess is a term used to broadly describe the upstream and downstream processes associated with the production of therapeutic products of interest from cultured cells. The cells can be, for example, mammalian, insect or microbial. Currently modern bioprocesses use a fed batch cell culture process almost exclusively to procure the products. In the fed batch cell culture process cells are typically inoculated into a cell culture medium under suspension and allowed to grow to a cell density sufficient to yield a product titer that is suitable for purification through a multistep chromatographic process. Continuous cell culture process is an alternative to the fed batch cell culture process. In the continuous cell culture process the cells are maintained at a high cell density for a much longer duration of time (e. g., >2 weeks) than the fed batch cell culture process. The continuous cell culture process is expected to provide several benefits over the fed batch culture by providing improvements in cost, agility and scale of manufacture.

Referring to FIG. 1 (PRIOR ART), there is a graph illustrating the benefits of the continuous cell culture process over the fed batch process (see E. Langer et al. "Continuous Bioprocessing and Perfusion: Wider Adoption coming as Bioprocessing Matures" Bioprocessing Journal. Spring 2014—the contents of this document are incorporated herein by reference for all purposes). Lines 102 and 104 respectively represent the theoretical yield of a product of interest, e.g., an antibody, and cell density for continuous cell culture process (perfusion cell culture process). Lines 106 and 108 respectively represent the antibody yield and cell density for the fed batch process. As can be seen, the antibody yields represented by lines 102 and 106 begin to separate after the two week point wherein the continuous culture product yield represented by line 102 begins an upward climb in yield and hence increased production benefits when compared to the fed batch product yield represented by line 106.

In the continuous cell culture process, cell retention is the most common way that practitioners use to maintain the cell density during the accumulation of the desired product. In cell retention, the cells are separated from spent media while fresh media is replaced as needed. Several techniques have been used to enable cell retention for performing the continuous cell culture process. In one technique, a spin filter is used where the spent media is extracted from the suspension culture by a filter that spins while having a membrane that separates the media from the cells. In another technique called alternating tangential flow filtration (ATF) a portion of the cells in the suspension broth are diverted into a tube where the cells are closed off from the main culture vessel while a moving membrane presses the liquid (spent media) through a cell retaining membrane. This active pumping system then re-opens and pushes the cells back into the culture while the spent media is siphoned away. Currently the ATF technique is dominant within the industry. These two cell retention techniques may work well but there is still a desire to improve and enhance the continuous cell culture process. One such improvement is the subject of the present disclosure.

SUMMARY

Disclosed herein is a perfusion bioreactor, and a method for using the perfusion bioreactor are described in the independent claims of the present disclosure. Advantageous embodiments of the perfusion bioreactor and the method for using the perfusion bioreactor are described in the dependent claims. In one aspect, the present disclosure provides a perfusion bioreactor comprising: (i) a vessel having at least one opening and a cavity; (ii) at least one lid attachable to the vessel to cover the at least opening; (iii) a porous membrane disposed within the cavity to divide the cavity into an inner compartment and an outer compartment; (iv) a fresh media port extending through the vessel or the at least one lid (e.g., the fresh media port is configured to receive a fresh media tube having an end located in the inner compartment); (v) a spent media port extending through the vessel or the at least one lid (e.g., the spent media port is configured to receive a spent media tube having an end located in the outer compartment); and, (vi) a mixer device. In embodiments, the mixer comprises an impeller and a shaft, wherein the impeller and the shaft are disposed within the inner compartment. The perfusion bioreactor may also have one or more other components including (for example) an inner vessel (which supports the porous membrane), a gas sparger port (which connects to a gas sparger), a bleed-off port (configured to receive a bleed-off line), a sensor port (which connects to a sensor), a spin filter (connected to the impeller device), a membrane clearing blade (connected to the mixer), a vent, and a gas permeable housing (in the vessel). In embodiments, the vessel or the porous membrane or both are flexible, making the perfusion bioreactor a flexible bag bioreactor.

In another aspect, the present disclosure provides a method for using a perfusion bioreactor to perform a continuous cell culture. The method comprises the steps of: (a) providing the perfusion bioreactor which comprises; (i) a vessel having at least one opening and a cavity; (ii) at least one lid attachable to the vessel to cover the at least one opening; (iii) a porous membrane disposed within the cavity to divide the cavity into an inner compartment and an outer compartment; (iv) a fresh media port extending through the vessel or the at least one lid, wherein the fresh media port is configured to receive a fresh media tube that has an end located in the inner compartment; (v) a spent media port extending through the vessel or the at least one lid, wherein the spent media port is configured to receive a spent media tube that has an end located in the outer compartment; and, (vi) a mixer; (b) adding cells to the inner compartment; (c) introducing fresh media through the fresh media tube into the inner compartment; (d) operating the impeller device to rotate the impeller within the inner compartment to enable transportation of spent media and cell secreted material (e.g., recombinant protein, antibody, virus particles, DNA, RNA, sugars, lipids, biodiesel, inorganic particles, butanol, metabolic byproducts) through the porous membrane into the outer compartment; and (e) removing the spent media and the cell secreted material through the spent media tube from the outer compartment. In embodiments, the mixer comprises an impeller device comprising an impeller and a shaft, wherein the impeller and the shaft are disposed within the inner compartment.

Additional aspects of the present disclosure will be set forth, in part, in the detailed description, figures and any claims which follow, and in part will be derived from the detailed description, or can be learned by practice of the disclosure. It is to be understood that both the foregoing general description and the following detailed description are exemplary and explanatory only and are not restrictive of the disclosure as disclosed.

BRIEF DESCRIPTION OF THE DRAWINGS

A more complete understanding of the present disclosure may be had by reference to the following detailed description when taken in conjunction with the accompanying drawings wherein:

FIGS. 5D1, 5D2 and 5D3 are illustrations of an experimental assembled perfusion bioreactor (FIG. 5D1) that underwent a test to prove that small molecules like food dye (dark colored liquid) when added into the inner vessel (FIG. 5D2) will pass from the inner vessel (inner compartment) through 10 micron woven mesh porous membranes into the outer compartment (FIG. 5D3);

FIG. 5F1 is an illustration of an experimental set-up to test the feasibility of an experimental perfusion bioreactor in accordance with an embodiment of the present disclosure;

FIG. 5F2 is a graph illustrating the results of an experiment conducted using the experimental set-up and experimental perfusion bioreactor shown in FIG. 5F1;

DETAILED DESCRIPTION

Figure 1:
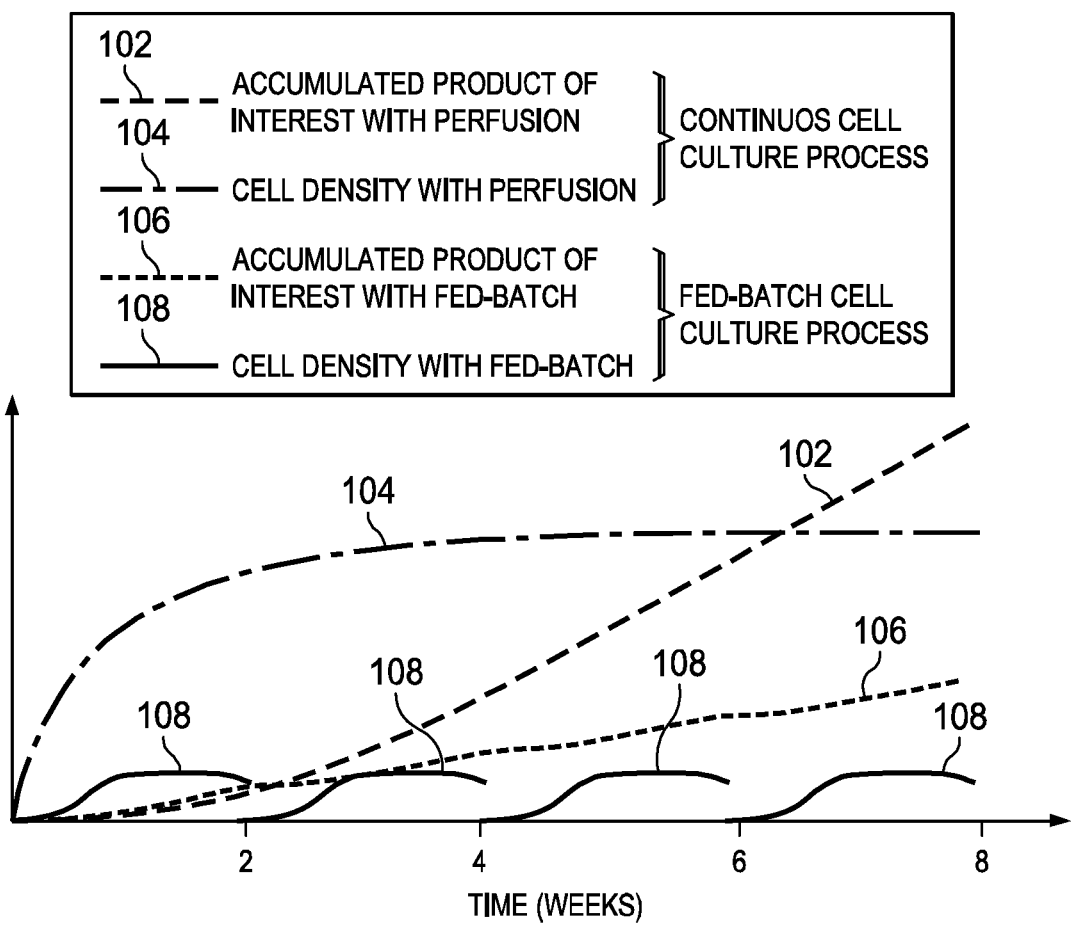
FIG. 1 (PRIOR ART) is a graph which illustrates the benefits of the continuous cell culture process over the fed batch process.

Disclosed herein is a new perfusion bioreactor which is configured for performing a continuous cell culture. The new perfusion bioreactor comprises: (i) a vessel having at least one opening and a cavity; (ii) at least one lid attachable to the vessel to cover the at least one opening; (iii) a porous membrane disposed within the cavity to divide the cavity into an inner compartment and an outer compartment; (iv) a fresh media port extending through the vessel or the at least one lid, wherein the fresh media port is configured to receive a fresh media tube that has an end located in the inner compartment; (v) a spent media port extending through the vessel or the at least one lid, wherein the spent media port is configured to receive a spent media tube that has an end located in the outer compartment; and, (vi) a mixer. In embodiments, the mixer comprises an impeller device comprising an impeller and a shaft, wherein the impeller and the shaft are disposed within the inner compartment. As described in detail below, the perfusion bioreactor may also have one or more other components including, for example, an inner vessel (which supports the porous membrane or multiple porous membranes), a bleed-off port (configured to receive a bleed-off line), a sensor port (connected to a sensor), a gas sparger port (connected to a gas sparger), and a spin filter.

Also disclosed herein is a method for using the new perfusion bioreactor to perform a continuous cell culture. The method comprises the steps of: (i) providing the new perfusion bioreactor; (ii) adding cells to the inner compartment; (iii) introducing fresh media through the fresh media tube into the inner compartment; (iv) operating the mixer device to provide agitation to the contents of the inner to enable transportation of spent media and cell products or secreted material (e.g., recombinant protein, antibody, virus particles, DNA, RNA, sugars, lipids, biodiesel, inorganic particles, butanol, metabolic byproducts) through the porous membrane into the outer compartment; and (v) removing the spent media and the cell secreted material through the spent media tube from the outer compartment. The new perfusion bioreactor is a marked improvement over the traditional cell culture bioreactor which needs to be accompanied by a separate filtration unit as part of the setup to separate the nutrients from the cells and other bio-media.

Various embodiments of the present disclosure will be discussed with reference to FIGS. 2-9, which illustrate various new perfusion bioreactors and methods for using the various new perfusion bioreactors according to non-limiting embodiments of the present disclosure. The following description is intended to provide an enabling description of the new perfusion bioreactor and the various aspects of the new perfusion bioreactor will be specifically discussed in detail throughout the disclosure with reference to the non-limiting embodiments, these embodiments are interchangeable with one another within the context of the disclosure. Although the various new perfusion bioreactor described herein are done with reference to separating cell secreted recombinant proteins from cells in a liquid (media) it should be appreciated that the new perfusion bioreactor can be used in other applications which involve different analytes as well such as (for example): biodiesel, inorganic particles such as quantum dots, antigens, extracts, metabolic by products like alcohol, enzymes; and therapeutic oncolytic viruses.

Figure 2:
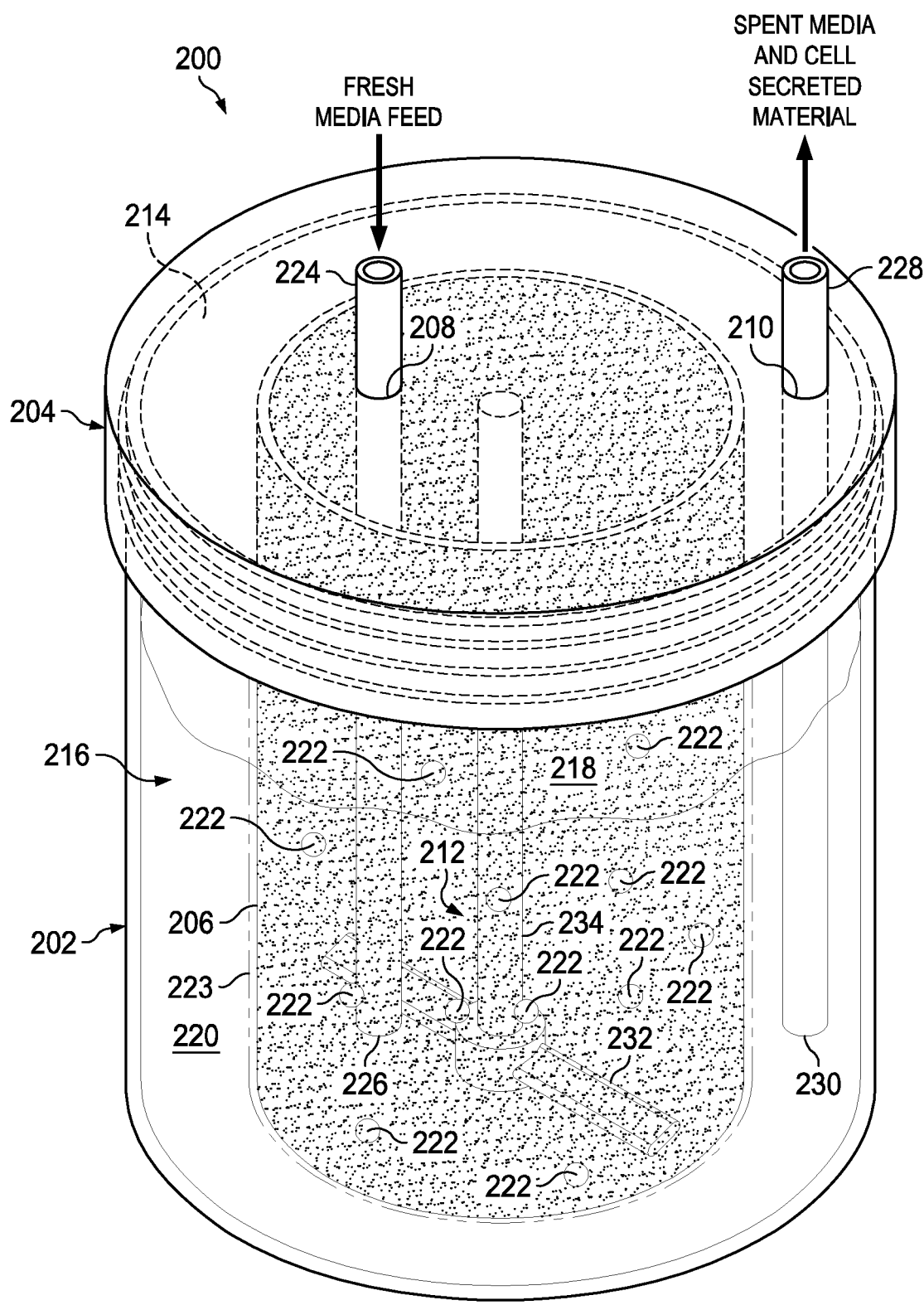
FIG. 2 is a schematic illustrating the basic components of a perfusion bioreactor in accordance with an embodiment of the present disclosure.

Referring to FIG. 2, there is a schematic illustrating the basic components of a perfusion bioreactor 200 in accordance with an embodiment of the present disclosure. As shown, the perfusion bioreactor 200 includes a vessel 202, an optional lid 204, a porous membrane 206, a fresh media port 208, a spent media port, 210, and a mixer device 212. The vessel 202 (e.g., transparent vessel 202) has an opening 214 and a cavity 216. The lid 204 is attachable (e.g., screwed, pushed-on) to the vessel 202 in order to cover the opening 214. The external vessel 202 can be plastic, glass, ceramic or stainless steel. The porous membrane 206 is disposed within the cavity 216 in a manner to divide the cavity 216 into an inner compartment 218 and an outer compartment 220. In this example, the porous membrane 206 has enough structural integrity to not collapse and get tangled with the mixer device 212 (see below for a discussion about an exemplary way that the porous membrane 206 can be incorporated into an inner vessel 246). The impeller can be designed to optimize motional transport across the porous membrane. The inner compartment and the outer compartment can both or each contain motional stirrers or impellers. The impeller design can be tailored to maximize motional transport along the membrane regions while yielding the proper cell agitation. For example, an impeller that has blades which run parallel along the length of the cell permeable membrane but do not touch can be made. The mechanical motion of pushing media into the mesh without damaging cells is the desired effect. The vessel can also contain a spin filter. In embodiments, the vessel 202 or the porous membrane 206 may be rigid containers or one or both of these elements may be flexible bags.

The porous membrane 206 is semi-permeable so as to contain fresh media and cells 222 (not to scale and not indicative of quantity of cells 222) within the inner compartment 218 and allow spent media with cell secreted material (e.g., recombinant protein, antibody, virus particles, DNA, RNA, sugars, lipids, biodiesel, inorganic particles, butanol, metabolic byproducts) to pass through into the outer compartment 220. The porous membrane 206 can be tailored for the size of the cells 222 so that cell retention is optimum. For instance, the porous membrane 206 can have pores therein with sizes ranging from about 0.5 to about 150 microns. Further, the porous membrane 206 can have an inert coating 223 (e.g., Pluronic F127, SigmaCote™) applied thereto to help prevent bio-fouling of the pores with media, cells, cell secreted material etc. In embodiments, the porous membrane can be made of plastics such as, for example, nylon, polytetrafluoroethylene (PTFE), polyester, Polystyrene, polypropylene, polycarbonate Cyclic olefin co-polymers (COP), cellulose, Ultem 1000. The porous membrane could be also be ceramic or stainless steel or glass. The porous membrane can be affixed to the inner vessel (which may have viewing window(s)) by a wide-variety of methods including, for example, injection over-molding, adhesives, laminate membranes, spot welding, laser sintering, and ultrasonic welding. The porous membrane can be coated with an inerting non-biofouling surface treatment such as, for example, pluronic F68, Aculon Nanoclear or Aculon multisurface hydrophobic coating, Pluronic F127 or Sigma-Cote™. Anti-fouling chemistry on semi-porous membrane can help mitigate time to fouling. The porous membrane can be patterned to contain surface geometry that minimize bio-fouling. The porous membranes can be designed and tailored for cell sizes. A membrane clearing blade is used to clean the porous membrane(s) to prevent bio-fouling of the porous membrane(s). It should be appreciated that some polymer membranes can foul easier than others, where polycarbonate has appeared to be the least fouling. Ultrasonic welding and heat sealing can be used for the porous membrane attachment to the inner vessel. The porous membrane can be tailored for the cell size so that cell retention is optimum. The porous membrane can have a pore density >2% where pore size of 12 microns appears to work well in some applications. The porous membrane can be located on the sides of the inner vessel or on the bottom or even on the top most portion of the inner vessel. The top membrane design may be the best at avoiding routine cell to membrane contact. In embodiments, the vessel or the porous membrane or both are flexible, making the perfusion bioreactor a flexible bag bioreactor.

Figure 4:
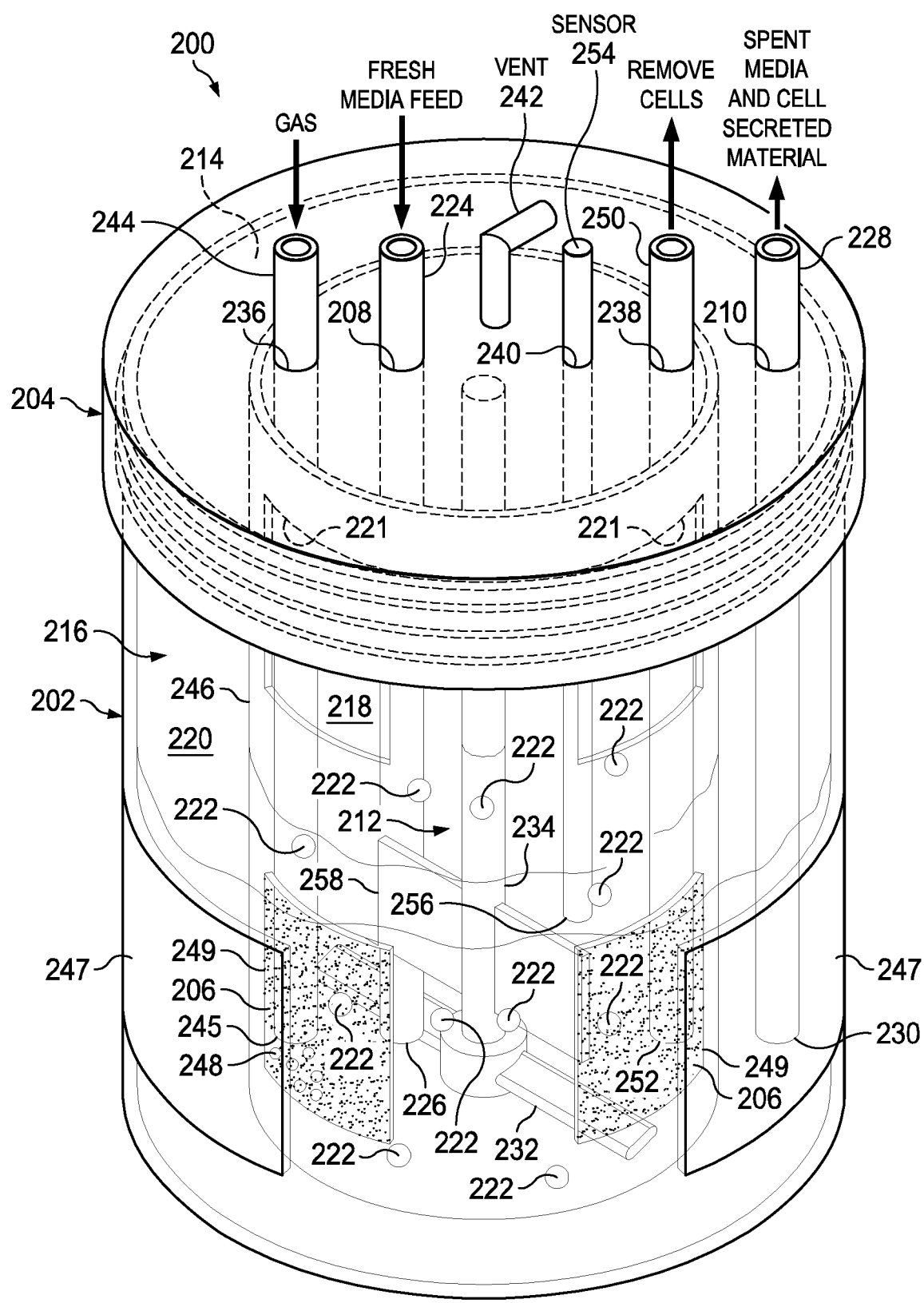
FIG. 4 is a schematic illustrating the perfusion bioreactor shown in FIG. 2 including some additional components in accordance with an embodiment of the present disclosure.
Figure 5A:
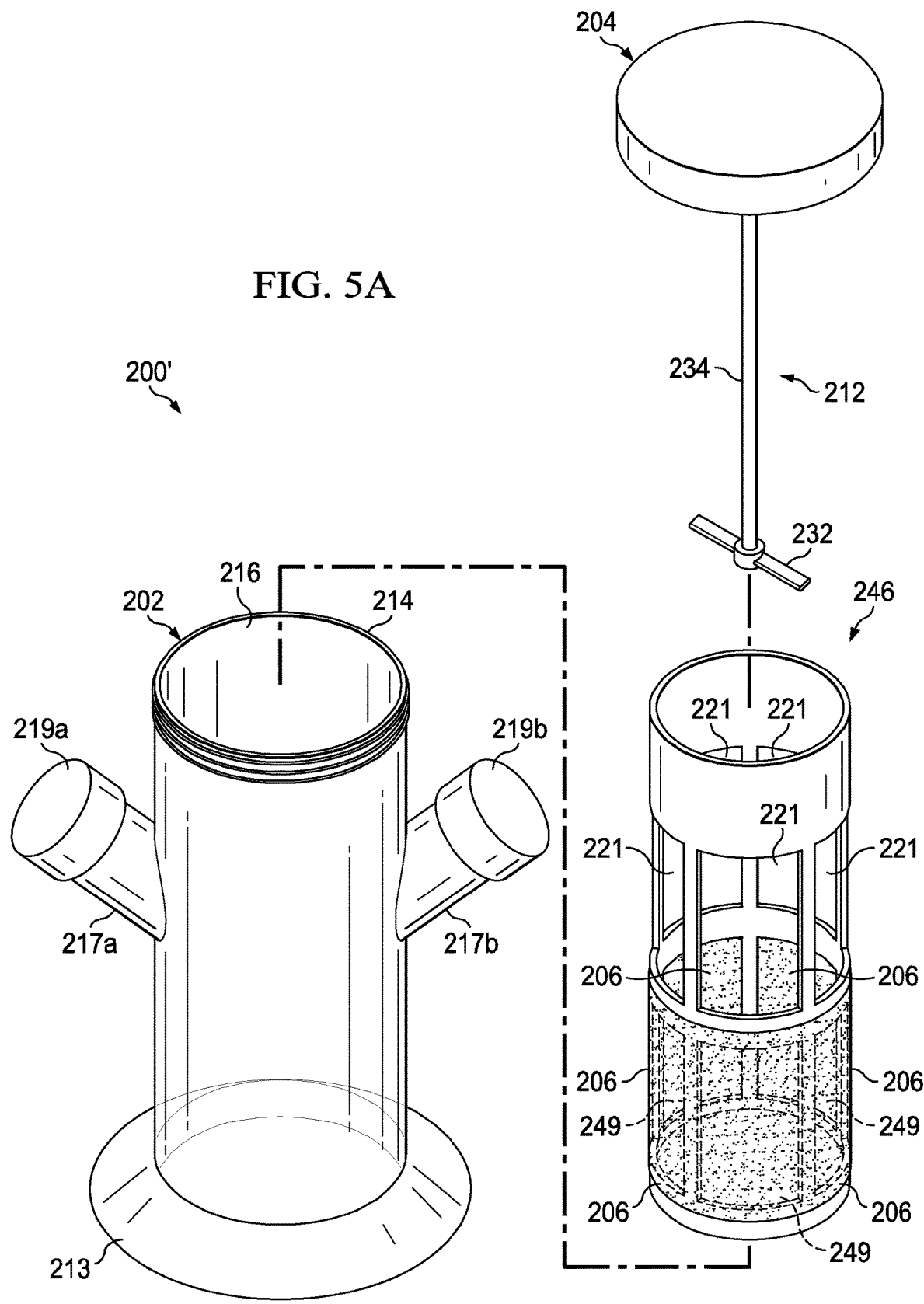
FIG. 5A is an illustration of a disassembled experimental perfusion bioreactor in accordance with an embodiment of the present disclosure.
Figure 5B:
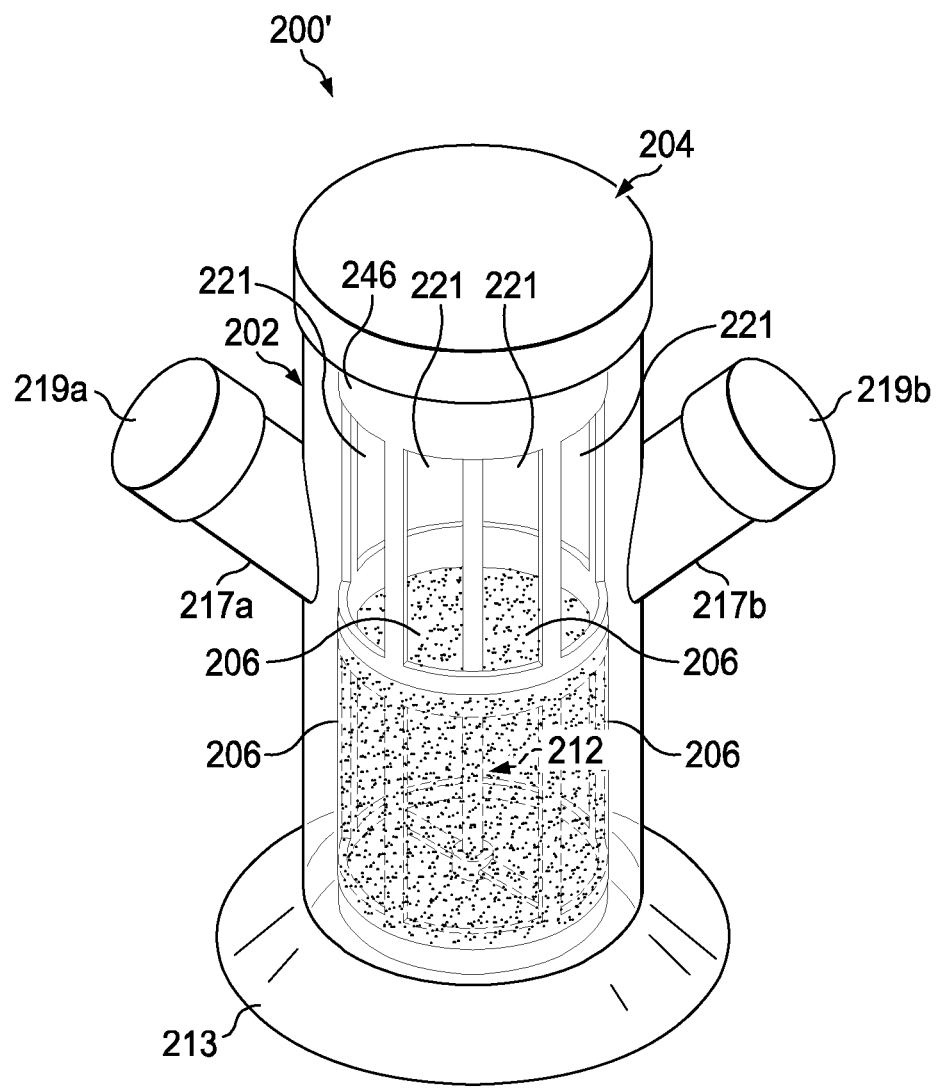
FIG. 5B is an illustration of an assembled experimental perfusion bioreactor in accordance with an embodiment of the present disclosure.
Figure 5C:
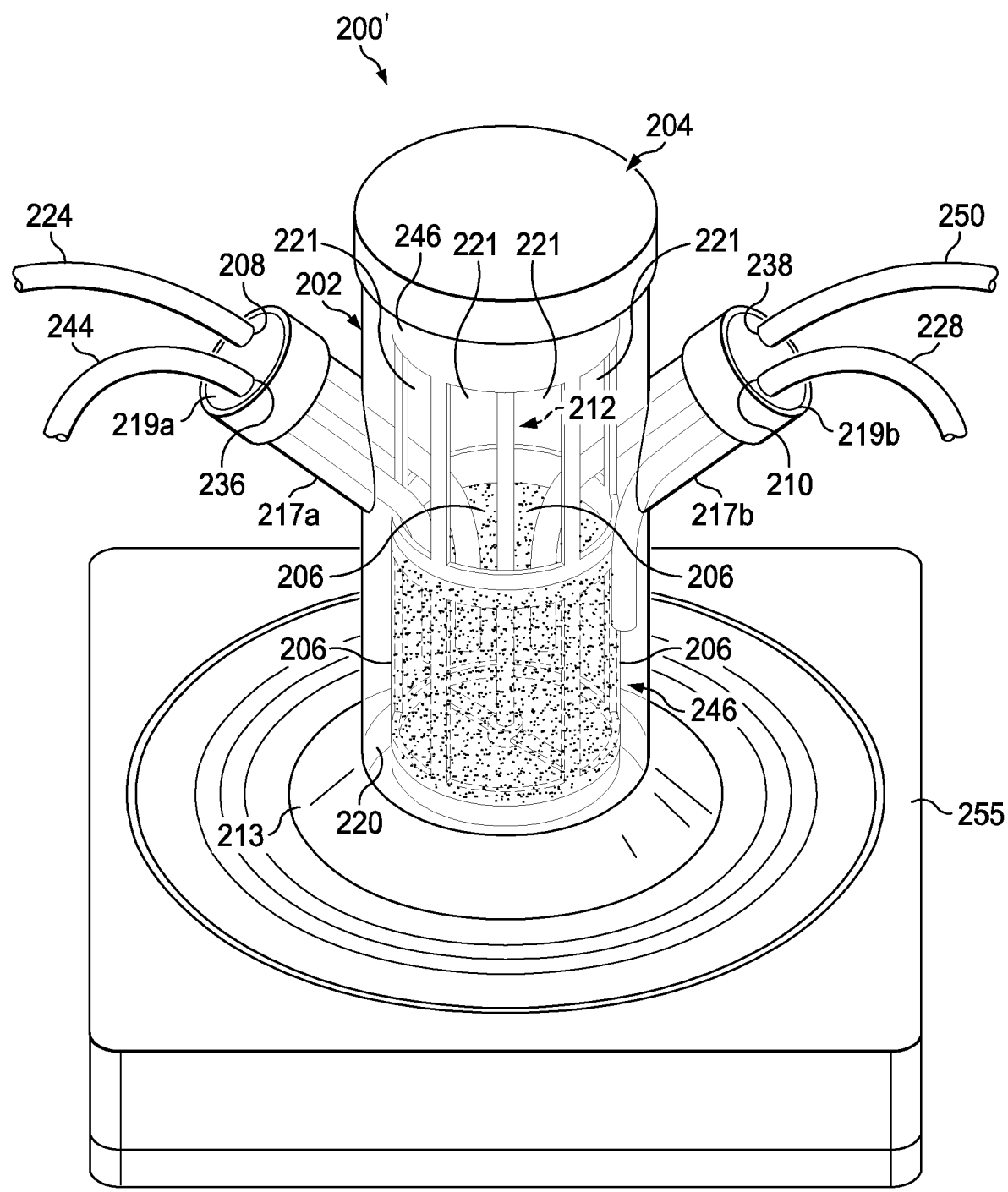
FIG. 5C is an illustration of an assembled experimental perfusion bioreactor in accordance with an embodiment of the present disclosure.

As shown, the fresh media port 208 and the spent media port 210 both extend through the lid 204 but if desired could extend through the vessel 202 as shown, for example, in FIG. 5C. The fresh media port 208 is configured to receive a fresh media tube 224 that has an end 226 located in the inner compartment 218. The fresh media tube 224 is used to supply fresh media to the inner compartment 218. The spent media port 210 is configured to receive a spent media tube 228 that has an end 230 located in the outer compartment 220. The spent media tube 228 is used to remove the spent media and the cell secreted material (e.g., recombinant protein, antibody, virus particles, DNA, RNA, sugars, lipids, biodiesel, inorganic particles, butanol, metabolic byproducts) from the outer compartment 220. As shown in FIG. 5C, the impeller device 212 includes an impeller 232 and a shaft 234. The impeller 232 and the shaft 234 are both disposed within the inner compartment 218. In this example, the impeller 232 is attached to one end of the shaft 234 while another end of the shaft 234 is rotatably attached to and extends downward from the removable lid 104. The impeller 232 would be rotated by a magnetic stir plate 255 located under the vessel 202 (see FIG. 5C for example of the magnetic stir plate 255). Alternatively, the mixer device 212 may have a boat style top down driven impeller 232. Or, the mixer may be a levitating stir element, a magnetic stir element, a paddle-like stirring element. In embodiments, any suitable stirring devices may be used. The perfusion bioreactor 200 may also have one or more additional components (e.g., inner vessel (which supports the porous membrane 206 or multiple porous membranes), bleed-off port 238 (configured to receive a bleed-off tube 250), sensor port 240 (connected to a sensor 254), gas sparger port 236 (connected to a gas sparger 244), spin filter 243 etc. . . . ) as described below with respect to FIGS. 3-4. The inner vessel could contain reconstituted media so that all the end-user needs to do is add sterile water and cells. Microcarrier beads can also used or provided within the vessel for high density adherent cell culture.

Figure 3:
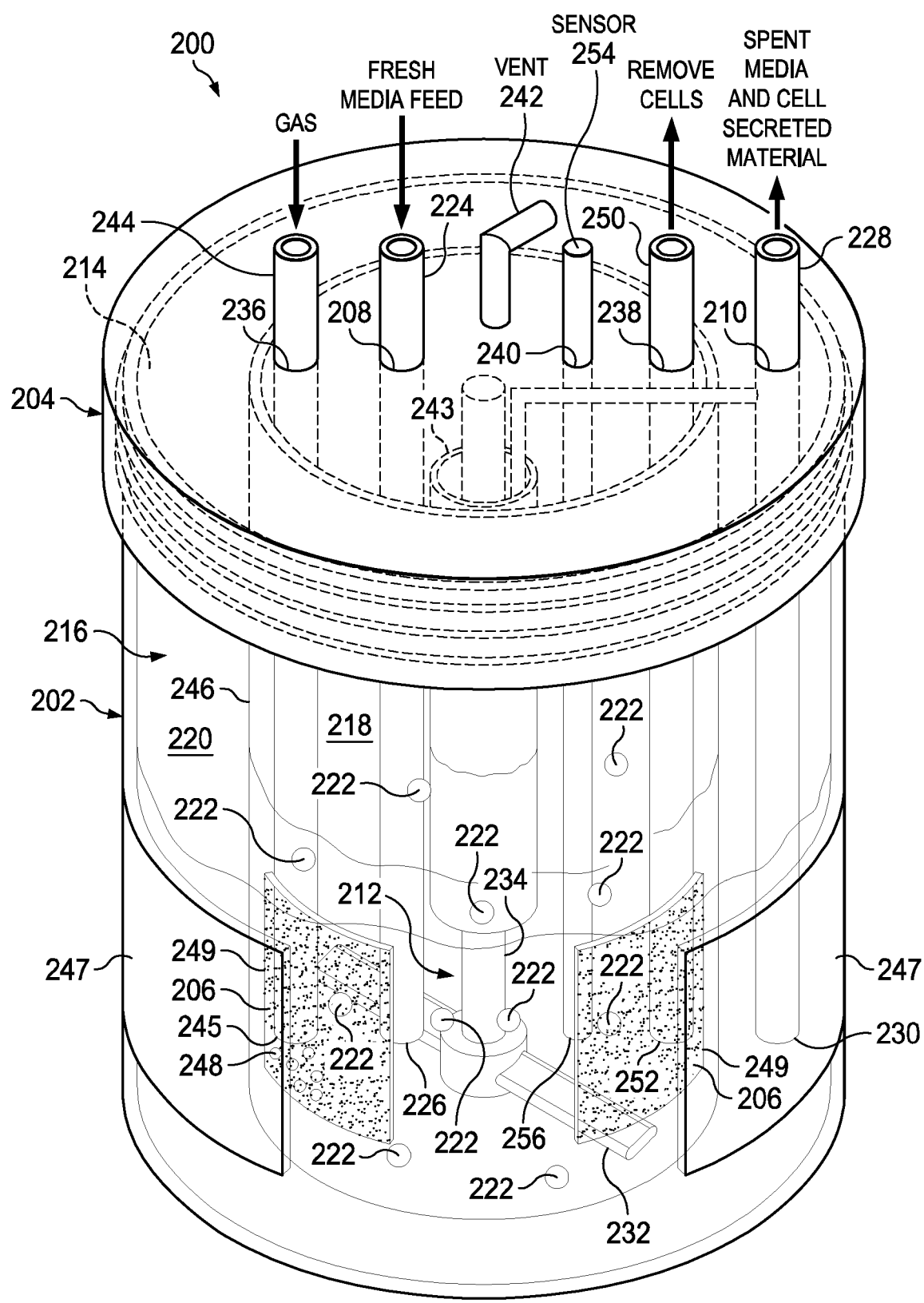
FIG. 3 is a schematic illustrating the perfusion bioreactor shown in FIG. 2 including some additional components in accordance with an embodiment of the present disclosure.

Referring to FIG. 3, there is a schematic illustrating the perfusion bioreactor 200 shown in FIG. 2 including some additional components in accordance with embodiments of the present disclosure. None, one, some or all of these additional components may be present in embodiments. The perfusion bioreactor 200 includes the aforementioned basic components namely the vessel 202 (with opening 214 and cavity 216), the lid 204, the porous membrane 206 (which may be multiple porous membranes 206), the fresh media port 208 (having the fresh media tube 224 inserted therein), a spent media port, 210 (having the spent media tube 228 inserted therein), and the mixer device 212 (as shown, an impeller 232 and shaft 234). In addition, the perfusion bioreactor 200 can include one or more additional components such as a gas sparger port 236, a bleed-off port 238, a sensor port 240, a vent 242, a spin filter 243, an inner vessel 246 (configured to support one or more porous membranes 206), and a gas permeable housing material 247 incorporated into the side of the vessel 202. Gas sparging devices and a wide range of sensors (e.g., temperature, $DO_2$, $CO_2$, pH, cell density) can be added to one or both the inner compartment and the outer compartment for continuous multivariate QbD and process analytical technology (PAT) design and operation. A gas permeable film such as fluorinated ethylene polypropylene (FEP) optically clear film made with Teflon® fluoropolymers can be integrated into the external housing of the bioreactor's vessel and lid if desired for improving oxygenation to the cultured cells.

In this example, the gas sparger port 236, the bleed-off port 238, the sensor port 240, and the vent 242 each extend through the lid 204 but if desired could extend through the vessel 202. The gas sparger port 236 is connected to a gas sparger 244 that has one end 245 located in the inner compartment 218 or the outer compartment 220. The gas sparger 244 is used to add oxygen (indicated by clear bubbles 248) to the media in inner compartment 218 (as shown) or the outer compartment 220 (not shown). The bleed-off port 238 is configured to receive a bleed-off tube 250 that has an end 252 located in the inner compartment 218. The bleed-off tube 250 is used to remove cells 222 from the inner compartment 218 to control the cell density. The sensor port 240 is connected to a sensor 254 that has an end 256 located in the inner compartment 218 (as shown) or the outer compartment 220 (not shown). For example, the sensor 254 can be a: dissolved oxygen ($DO_2$) sensor, a carbon dioxide ($CO_2$) sensor, a pH sensor, a cell density sensor, a glucose sensor, or a flow or shear stress and temperature sensor, or any other sensor. In embodiments, the spin filter 243 is connected to the shaft 234 of the mixer device 212. The spin filter 243 is used to provide additional filtration of spent media wherein the spent media and cell secreted material can be removed therefrom via for example the spent media tube 228. The inner vessel 246 can have one or more openings 249 therein used to support one or more porous membranes 206 (note: two openings 249 and two porous membranes 206 are illustrated in FIG. 3). The inner vessel 246 is sized to fit within the cavity 216 of the vessel 202. Further, the vessel 202, which may include an optically clear gas permeable house material 247 (e.g., silicones (like PDMS), polystyrene, polyethylene, polyester, polymethylpentene, polytetrafluoroethylene, polycarbonate and silicone-polycarbonate co-polymers, polyacrylate, polyurethane, nylon, non-woven rayon, ethyl cellulose, cellulose acetate, fluorinated ethylene propylene (FEP)), can be integrated into the external housing of the vessel 202 for providing additional oxygenation to the cell media. Moreover, the inner vessel 246 can be transparent so as to provide viewing window(s) between the porous membranes 206 to enable the visual inspection of the cell culture. In additional embodiments the perfusion bioreactor may include a pressure drop provided by a pressure inlet and a vacuum pressure outlet (see items 802 and 804 in FIG. 8A). The inner vessel may have one or more intervening windows placed between the porous membrane(s) to allow continuous visual inspection of the cell culture and media. The porous membrane can be located on the sides of the inner vessel or on the bottom or even on the top most portion of the inner vessel. The top membrane design may be the best at avoiding routine cell to membrane contact.

Referring to FIG. 4, there is a schematic illustrating the perfusion bioreactor 200 shown in FIG. 2 including some additional components in accordance with an embodiment of the present disclosure. None, some or all of these additional components may be present in embodiments, alone or in addition to none, some or all of the additional components shown in FIG. 3. In additional embodiments the perfusion bioreactor may have multiple inner vessels arranged in a "Russian Doll" arrangement, one inside another, each containing different populations of cells, to allow for co-culture in the perfusion device. The perfusion bioreactor 200 includes the aforementioned basic components namely the vessel 202 (with opening 214 and cavity 216), the lid 204, the porous membrane 206 (which may be multiple porous membranes 206), the fresh media port 208 (having the fresh media tube 224 inserted therein), a spent media port, 210 (having the spent media tube 228 inserted therein), and the mixer device 212 (with impeller 232 and shaft 234). In addition, the perfusion bioreactor 200 can include one or more additional components such as a gas sparger port 236, a bleed-off port 238, a sensor port 240, a vent 242, a membrane clearing blade 258, and an inner vessel 246 (configured to support one or more porous membranes 206). In this example, the gas sparger port 236, the bleed-off port 238, the sensor port 240, and the vent 242 each extend through the lid 204 but if desired could extend through the vessel 202. The gas sparger port 236 is connected to a gas sparger 244 that has one end 245 located in the inner compartment 218 (as shown) or the outer compartment 220 (not shown). The gas sparger 244 is used to add oxygen (indicated by clear bubbles 248) to the media in inner compartment 218. The bleed-off port 238 is configured to receive a bleed-off tube 250 that has an end 252 located in the inner compartment 218. The bleed-off tube 250 is used to remove cells from the inner compartment 218 to control the cell density. The sensor port 240 is connected to a sensor 254 that has an end 256 located in the inner compartment 218 (as shown) or the outer compartment 220 (not shown). For example, the sensor 254 can be: a $DO_2$ sensor, a $CO_2$ sensor, a pH sensor, a cell density sensor, a glucose sensor, a flow or shear stress and temperature sensor, or any other sensor. In embodiments, the membrane clearing blade 258 is attached to the shaft 234 of the mixer device 212. The membrane clearing blade 258 is used to clean the porous membrane(s) 206 by gently brushing the porous membrane(s) 206 to prevent bio-fouling of the porous membrane(s) 206 (note: the inner vessel 246 could also have moving or rotating walls that help prevent cells 222 from attaching thereto). The inner vessel 246 can have one or more openings 249 therein used to support one or more porous membranes 206 (note: two openings 249 and two porous membranes 206 are illustrated in FIG. 4). Further, the inner vessel 246 may have one or more air exchange windows 221 (two shown). The inner vessel 246 is sized to fit within the cavity 216 of the vessel 202. Moreover, the inner vessel 246 can be transparent so as to provide viewing window(s) between the porous membranes 206 to enable the visual inspection of the cell culture.

It should be appreciated that the additional components such as the spin filter 243 (shown in FIG. 3) (rather than the membrane cleaning blade 258) and the gas permeable house material 247 can be used in the perfusion bioreactor 200 shown in FIG. 4. Further, it should be appreciated that the membrane cleaning blade 258 (rather than the spin filter 243) and the inner vessel 246 with one or more air exchange windows 221 may be used in the perfusion bioreactor 200 shown in FIG. 3. Basically, the additional components shown in FIGS. 3 and 4 are interchangeable and one or more of them may be used if desired in the perfusion bioreactor 200 shown in FIG. 2.

Referring to FIGS. 5A-5F2, there are several diagrams illustrating an experimental perfusion bioreactor 200' and various experimental setups used to test the experimental perfusion bioreactor 200' in accordance with an embodiment of the present disclosure. As shown in FIG. 5A, the perfusion bioreactor 200' when disassembled includes three components namely: (1) a lid 204 with a mixer device 212 (having a shaft 234 and an impeller 232) rotatably attached thereto and extending downward therefrom; (2) an inner vessel 246 with multiple openings 249 (five shown) used to support multiple porous membranes 206 (five shown) and multiple air exchange windows 221 (five shown); and (3) a vessel 202 including an opening 214, a cavity 216, a support plate 213, and two necks 217a and 217b (with corresponding two caps 219a and 219b) extending outward from the vessel 202. The perfusion bioreactor 200' can be assembled by placing the inner vessel 246 within the vessel 202 and then securing the lid 204 onto the vessel 202 such that the impeller device 212 (i.e., the impeller 232 and shaft 234) is located within the inner vessel 246 (see FIG. 5B).

In embodiments, the lid 204 may be removably attached to the vessel, or may be permanently attached to the vessel. In embodiments, then lid is integral to the vessel, allowing the perfusion bioreactor, once assembled, to be a closed, integral device. Or, alternatively, the lid when removable allows the perfusion bioreactor to be disassembled by the user and the contents to be accessed by the user.

Further, the perfusion bioreactor 200' when used will have caps 219a and 219b configured to have the fresh media port 208 (i.e., hole 208 sized to accept the fresh media tube 224), and the spent media port 210 (i.e., hole 210 sized to accept the spent media tube 228), and if desired one or more of the following: the gas sparger port 236 (connected to the gas sparger 244), the bleed-off port 238 (sized to accept the bleed-off tube 250), the sensor port 240 (connected to the sensor 254), and the vent 242. For example, FIG. 5C is a diagram of an exemplary perfusion bioreactor 200' where the cap 219a has the fresh media port 208 (which receives the fresh media tube 224) and the gas sparger port 236 (connected to the gas sparger 244) and the cap 219b has the spent media port 210 (which receives the spent media tube 228) and the bleed-off port 238 (which receives the bleed-off tube 250). The exemplary perfusion bioreactor 200' further has a magnetic stir plate 255 located external to the vessel 202. The magnetic stir plate 255 is configured to rotate the impeller 232 and the shaft 234.

In embodiments, the perfusion bioreactor shown in FIGS. 2-5D3 have significant advantages over currently available perfusion bioreactor systems. For example, The perfusion bioreactor has a semi-permeable membrane used to retain cells while allowing media to pass through. The presence of a porous membrane eliminates the need for traditional cell culture bioreactor's filtration units or other external devices such as Avoids external maintenance of an outside cell retention device like a centrifuge, tangential flow filtration (TFF) or Alternating Tangential Flow (ATF) (for example, see Refine technologies/Repligen device). The bioreactor can be operated continuously. The continuous operation of a 100 liter perfusion bioreactor can produce as much antibody as a 1000 liter traditional fed batch bioreactor. The perfusion bioreactor can enable cell growth beyond the typical 5-day batch cultivation with conventional sealed flask bioreactors. The perfusion bioreactor can be integrated with a continuous antibody or recombinant protein purification system. The perfusion bioreactor can be sold as just an insert for a re-use vessel or as a complete system. The assembled perfusion bioreactor can be gamma irradiated, e-beam sterilized, ultraviolet (UV) sterilized, ethanol sterilized or gas sterilized.

The perfusion bioreactor can be any size such as 0.1 liter to about 1000 liters or more. The perfusion bioreactor can be miniaturized to small scale like 15 ml volumes which could enable high throughput continuous culture assays. Currently the traditional AMBR bioreactor system is used to test fed batch cultures at the 15 ml volume level but is not currently capable of doing continuous cell culture scouting screens yet. With the new perfusion bioreactor this would be possible. The perfusion bioreactor could have fill a volume of 1 L to 3 L where the fresh media feed flow rates would be equal to one fill volume/day. The perfusion bioreactor can enable cell growth beyond the typical 5-day batch cultivation with conventional sealed flask bioreactors.

The perfusion bioreactor can be structured to optimize the availability of oxygen to the cells contained in the perfusion bioreactor. For example, a gas sparger, may be optionally used and/or a gas permeable film such as a FEP optically clear film made with Teflon® fluoropolymers can be integrated into the external housing of the bioreactor for providing additional oxygenation. The inner vessel can have one or more air exchange windows on a top portion of the inner vessel. The window(s) would be helpful in keeping oxygen to the cells.

The assembled perfusion bioreactor 200' was then tested in several experiments to show a proof-of-concept as described next with respect to FIGS. 5D1-5F2. In one experiment, the perfusion bioreactor 200' (see FIG. 5D1) underwent a test to prove the small molecules like food dye (dark colored liquid) when added into the inner vessel 246 (see FIG. 5D2) will pass from the inner vessel 246 through the 10 micron woven mesh porous membranes 206 (see FIG. 5D3). The test was a success in that the food dye added to the inner vessel 246 rapidly passed through the 10 micro woven mesh porous membranes 206.

Figure 5E:
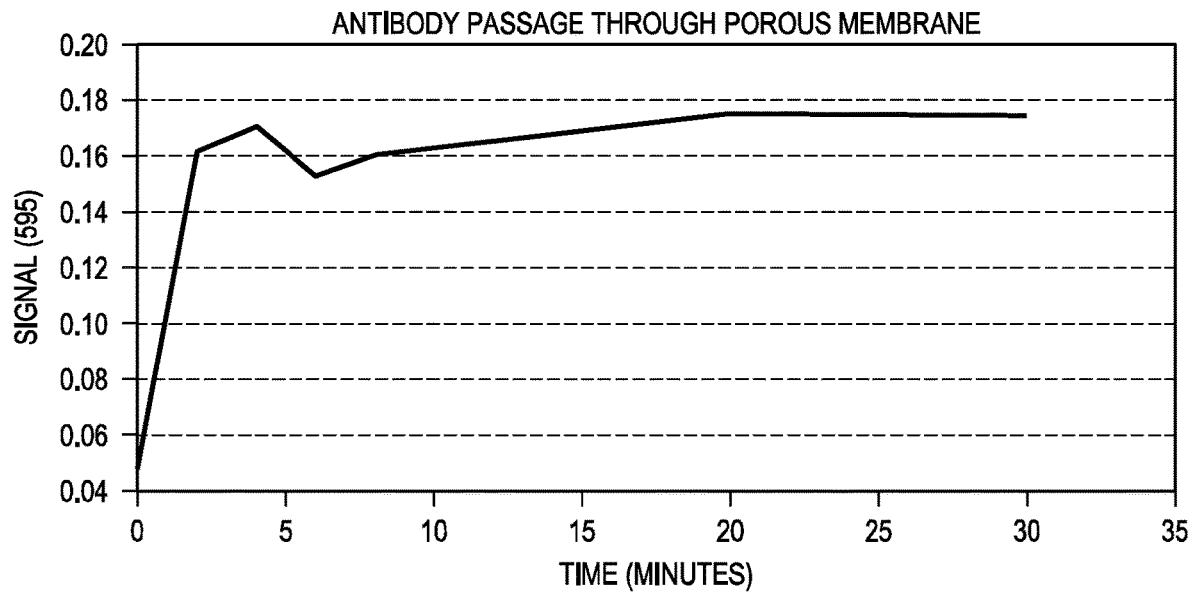
FIG. 5E is a graph illustrating a signal (y axis) versus time (x axis) associated with the passage of an antibody through 3 micron woven mesh porous membranes to test the feasibility of a perfusion bioreactor in accordance with an embodiment of the present disclosure.
Figure 5E:
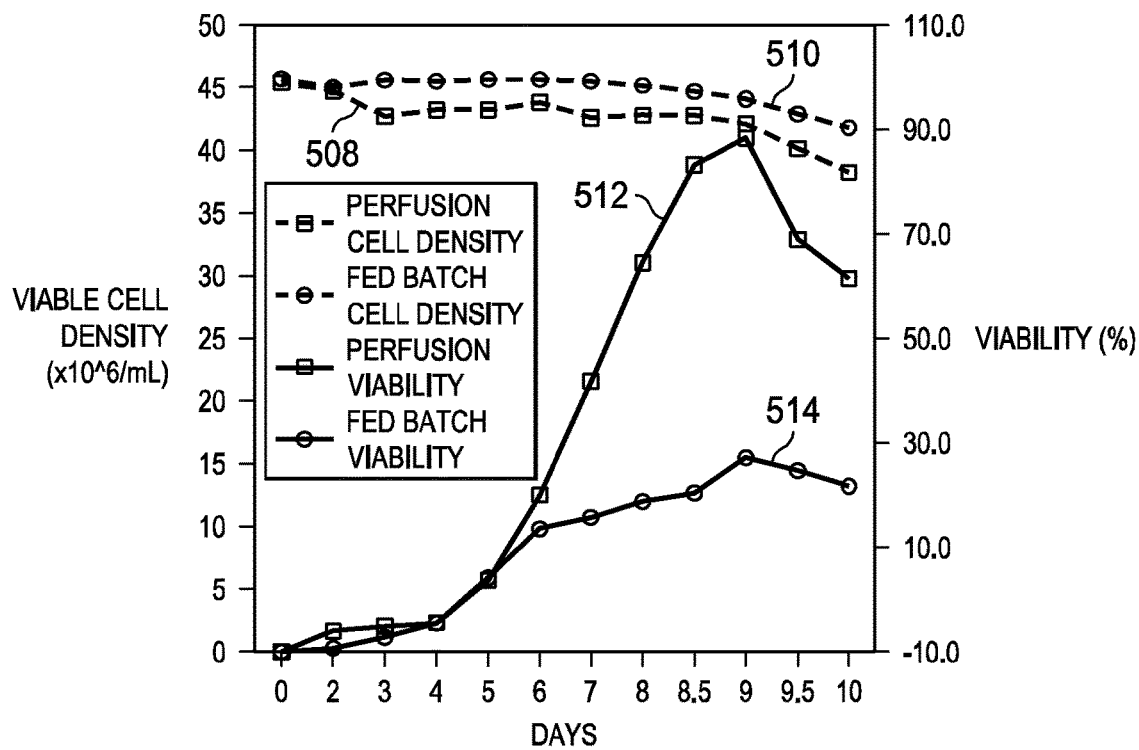

In another experiment, the inventors did not test the perfusion bioreactor 200' but did perform a test to prove that an antibody conjugate and spent media can pass through a 3 micron woven mesh porous membrane 206 (see FIG. 5E). In this experiment, the inventors spiked an alkaline phosphatase antibody conjugate on one side of a 3 micron woven mesh porous membrane 206 and demonstrated the rapid passage of the alkaline phosphatase antibody conjugate through the 3 micron woven mesh porous membrane 206. This demonstrates that an antibody as well as spent media will pass through a porous membrane 206 that has 3 micron pores.

In yet another experiment, the perfusion bioreactor 200' as shown in FIG. 5F1 was positioned inside of an incubator and a fresh media bottle 502 had its contents namely fresh media pumped by one pump head of a peristaltic pump 503 into the inner vessel 246 while the spent media and cell secreted material was pumped by another pump head of the peristaltic pump 503 out of the outer chamber 220 of the vessel 202 into the spent media bottle 504. An air pump 505, also called a sparger, and air flow meter 506 were used to help control the amount of aeration that the cells experience within the inner vessel 246. The magnetic stir plate 255 uses a rotating magnet therein to rotate the impeller 232 (not visible) within the inner vessel 246. FIG. 5F2 is a graph illustrating the results of this experiment where the graph shows two pieces of data (1) the viable cell density (see line 508 associated with the perfusion bioreactor 200' and line 510 associated with a fed batch culture device) and (2) % viability (see line 512 associated with the perfusion bioreactor 200' and line 514 associated with the fed batch culture device). The viable cell density is given in million cells per milliliter and compares the results of the perfusion bioreactor 200' (line 512) to the fed batch culture device (line 514). As can be seen from the graph the fed batch culture device could only reach ~15 million cells (line 514) while the perfusion bioreactor 200' went up to 40 million cells per milliliter (line 512). This indicates that the perfusion bioreactor 200' dramatically outperforms the fed batch culture device with respect to the cell density. The % viability shown in lines 508 and 510 was closely matching at ~90% between the perfusion bioreactor 200' and the fed batch culture device.

Figure 6:
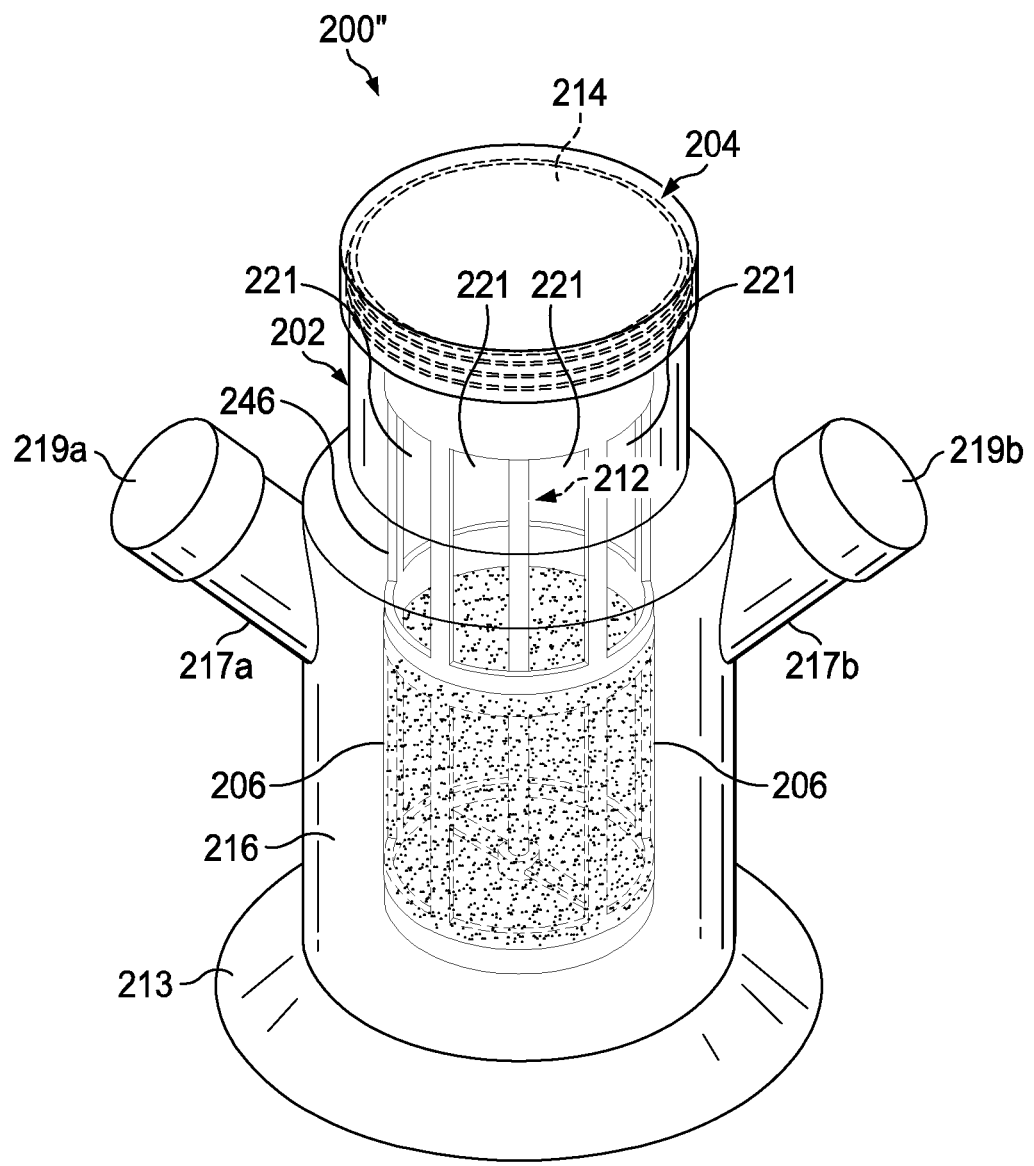
FIG. 6 is an illustration of an experimental assembled perfusion bioreactor in accordance with an embodiment of the present disclosure.

Referring to FIG. 6, there is a diagram illustrating an experimental perfusion bioreactor 200" in accordance with an embodiment of the present disclosure. As shown, the perfusion bioreactor 200" includes three components namely: (1) a lid 204 with an mixer device 212 rotatably attached thereto and extending downward therefrom; (2) an inner vessel 246 with multiple openings 249 (not visible) used to support multiple porous membranes 206 (visible as an opaque portion in diagram) and multiple air exchange windows 221; and (3) a vessel 202 including an opening 214, a cavity 216, a support plate 213, and two necks 217a and 217b (with corresponding two caps 219a and 219b) extending outward from the vessel 202. The perfusion bioreactor 200" was assembled by placing the inner vessel 246 within the vessel 202 and then securing the lid 204 onto the vessel 202 such that the mixer device 212 (i.e., the impeller 232 and shaft 234) is located within the inner vessel 246. Further, the perfusion bioreactor 200" when used will have caps 219a and 219b configured to have the fresh media port 208 (i.e., hole 208 sized to accept the fresh media tube 224), and the spent media port 210 (i.e., hole 210 sized to accept the spent media tube 228), and if desired one or more of the following: the gas sparger port 236 (i.e., hole 236 sized to connect to the gas sparger 244), the bleed-off port 238 (i.e., hole 238 sized to accept the bleed-off tube 250), the sensor port 240 (i.e., hole 240 sized to connect to the sensor 254), and the vent 242. It should be appreciated that the perfusion bioreactor 200' shown in FIGS. 5A-5F and the perfusion bioreactor 200" shown in FIG. 6 could be considered re-useable or single use, depending on the structure and material choices to make the devices. For example, a glass device could be considered reusable while a plastic device could be considered single-use. If desired, the perfusion bioreactors 200' and 200" may incorporate any one or more of the additional components 242, 244, 247, and 258 described above with respect to the aforementioned perfusion bioreactor 200.

An important component of the perfusion bioreactors 200, 200' and 200" is the porous membrane 206 which facilitates the separation of the inner compartment 218 (inner volume 218) and the outer compartment 220 (outer volume 220) and allows the extraction of the nutrient-depleted growth medium without allowing the cells to flow out of the vessel 202. The porous membrane 206 is specifically designed to retain within the inner compartment 218 the culture cells 222, for example, NS0 murine myeloma cells, PER. C6® human cells, Human Embryonic Kidney (HEK) 293, *Trichoderma reesei*, SF9, Chinese Hamster Ovary (CHO) cells 222, while allowing the spent media that contains the prospectively valuable cell secreted material (e.g., recombinant protein, antibody, virus particles, DNA, RNA, sugars, lipids, biodiesel, inorganic particles, butanol, metaboloic byproducts) to be passed through the porous membrane 206 into the outer compartment 220 for subsequent capture and purification. As discussed next, both analytical and numerical models have been used to size the pores of the porous membrane 206 and to calculate a pressure drop versus flow rate to prove the feasibility of the design of the aforementioned perfusion bioreactors 200, 200' and 200".

A. Darcy's Law Based Analytical Tool

Based on the theory of flow through porous media, the pressure drop across a porous membrane (such as the porous membrane 206) can be evaluated by the following analytical expression (1) that accounts for the flow resistance across the porous membrane due to viscous effects (Darcy term) and inertial effects:

$$\Delta p = \left(\frac{\mu}{K}u + C_2 \frac{1}{2}\rho u^2\right)\Delta t \quad (1)$$

$K$: permeability $C_2$: inertial resistance coefficient $\Delta t$: porpous layer thickness Therefore, the pressure drop is dependent on design variables related to the porous membrane, i.e., the thickness, $\Delta t$, permeability, $K$ and inertial resistance coefficient, $C_2$. The permeability K and inertial resistance coefficient $C_2$ can be determined from measurements of pressure drop vs. volume flow rate which are typically provided by the manufacturer of the porous membrane. In the absence of such measurements, the inertial loss term can be neglected and Darcy's law can be employed to calculate the pressure drop as a function of permeability as follows:

$$\Delta p = \frac{\mu}{K}u\Delta t \quad (2)$$

Figure 7:
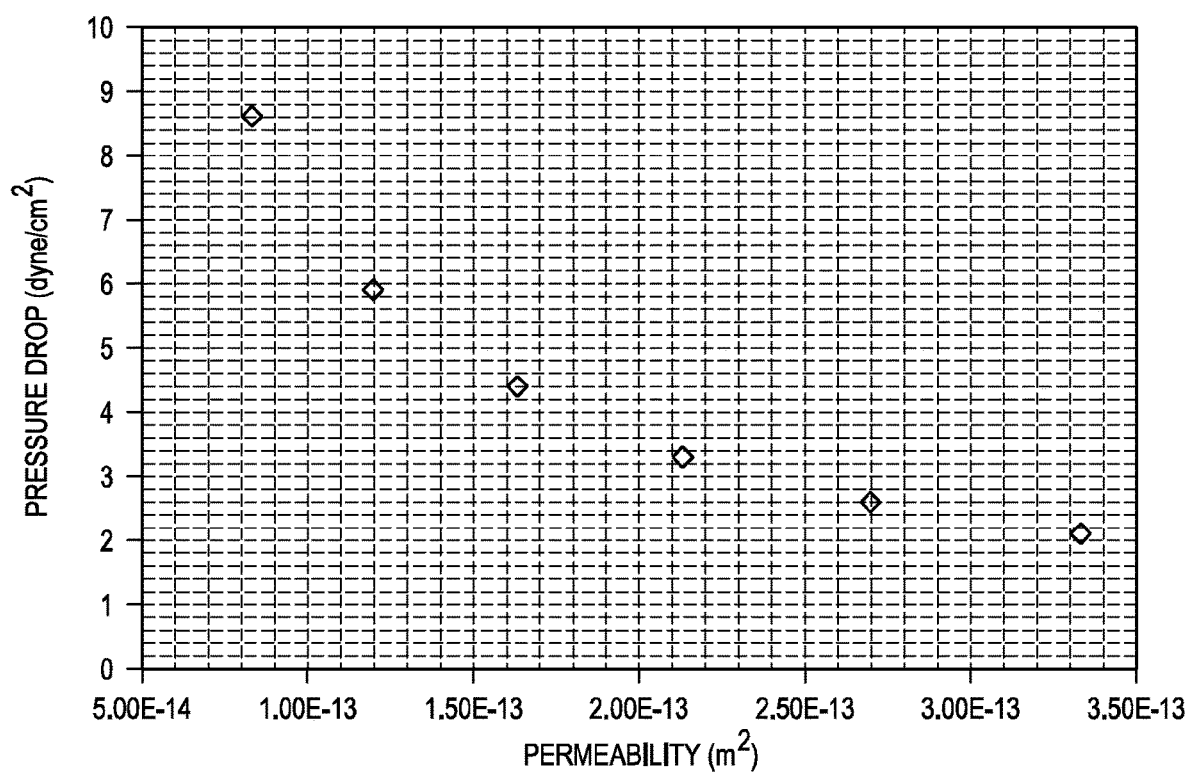
FIG. 7 is a graph illustrating a pressure drop (y axis) versus permeability (x axis) obtained from an analytical solution to show the feasibility of a perfusion bioreactor in accordance with the present disclosure.

Assuming a porous membrane thickness of 100 microns, and flow rate of 1 liter (L)/day, the pressure drop calculations based on equation (2) are shown in FIG. 7 which illustrates a graph of pressure drop (y axis) vs. membrane permeability (x axis). As shown in the graph, with increasing permeability resistance of the porous membrane there is a decrease of the flow across the porous membrane, which leads to lower pressure drops. The conclusion that can be derived from these analytical calculations is that for membrane permeability in the order of $10^{-13}$ m$^2$, which corresponds to pore size less than 10 microns, the pressure drop across the porous membrane is small. In other words, the data shows a very small pressure drop relative to membrane permeability. Hence, the use of a porous membrane should be very viable for media and molecular transport across the porous membrane during an extended cell culture in the perfusion bioreactor 200, 200' and 200".

B. Computational Fluid Dynamic (CFD) Model Developed in FLUENT

Figure 8A:
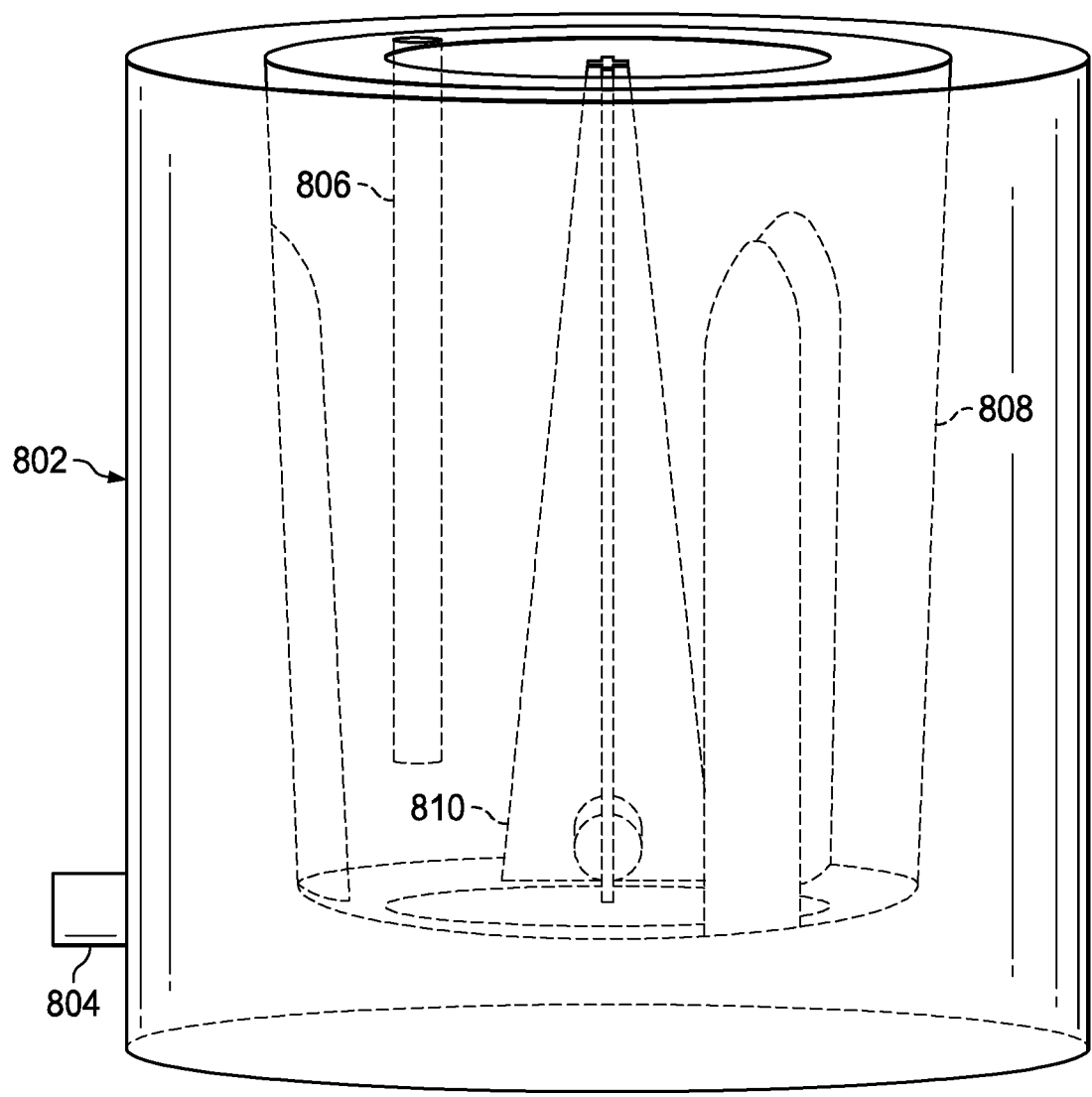
FIG. 8A is an illustration of a flow model setup in FLUENT used to show the feasibility of a perfusion bioreactor in accordance with the present disclosure.

In order to account for inertial effects due to the agitation of the growth medium by the mixer 232 in the perfusion bioreactor 200, 200' and 200", the inventors developed a CFD model that simulates the agitation process and calculates the pressure drop across the porous membrane 206. FIG. 8A illustrates the CFD model setup where the vessel is indicated by 802, the vacuum pressure outlet is indicated by 804, the pressure inlet (p=0) is indicated by 806, the porous membrane is indicated by 808 (flask wall: porous membrane (0.1 mm thick) treated as a porous jump boundary condition), and the mixer is indicated by 810. The CFD model shows the effects of motional stirring where the mixer 810 helps to enable the cell culture but also promote the transport of media across the porous membrane 808. This is an especially valuable attribute when one considers an extended cell culture and potential bio-fouling of the porous membrane(s) 206 within the perfusion bioreactor 200, 200' and 200".

Figure 8C:
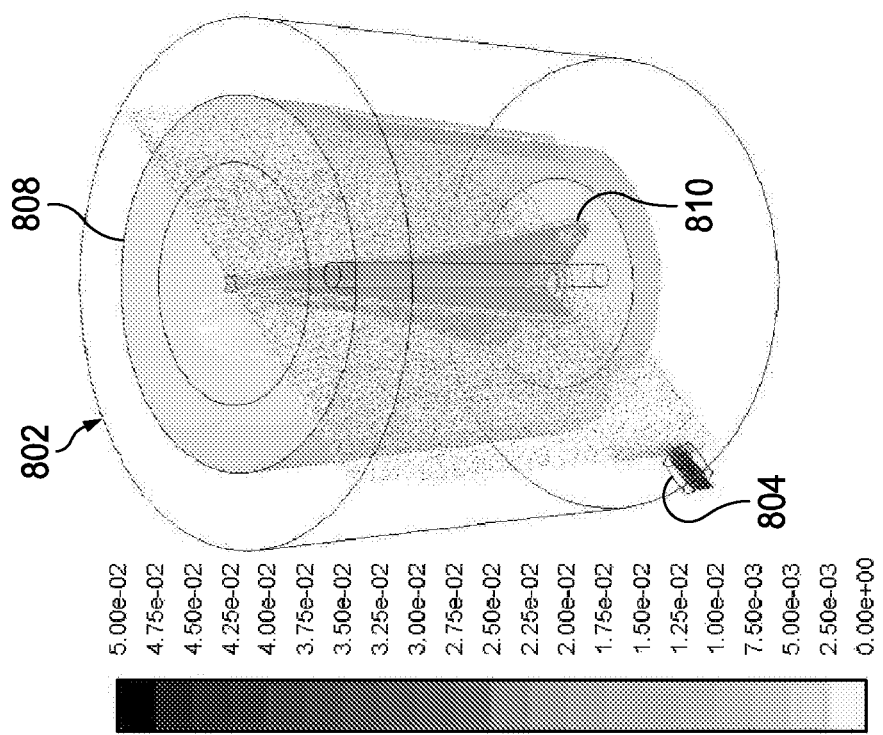
FIGS. 8B, 8C and 8D show the FLUENT model results indicating the velocity vectors grey scale shaded by the velocity magnitude are indicated at the horizontal plane (FIGS. 8B and 8D) and the vertical plane (FIG. 8C) which show the feasibility of a perfusion bioreactor in accordance with the present disclosure.
Figure 8B:
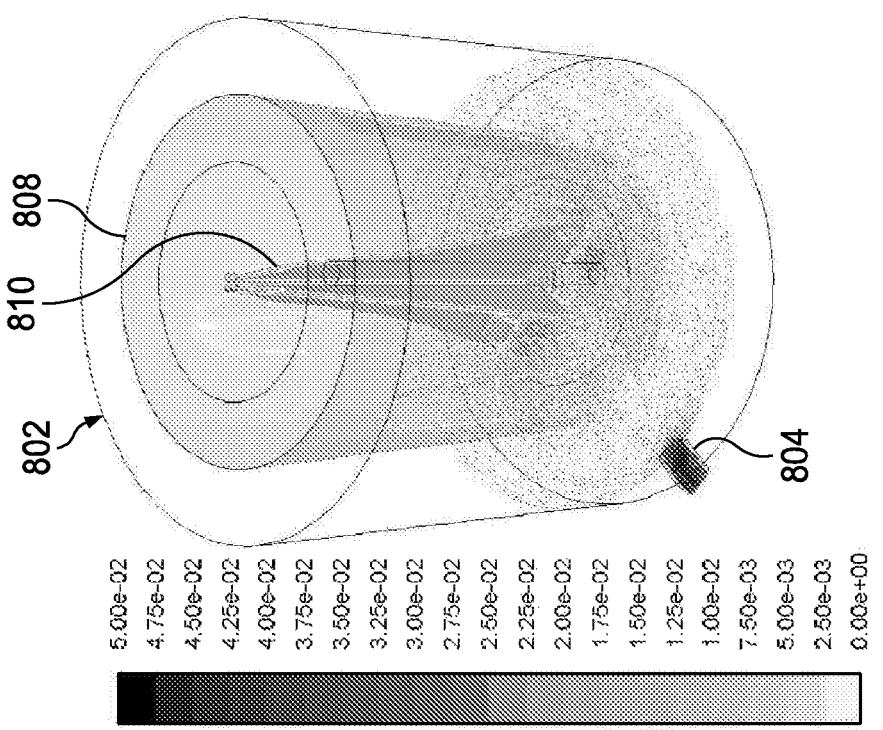
Figure 8D:
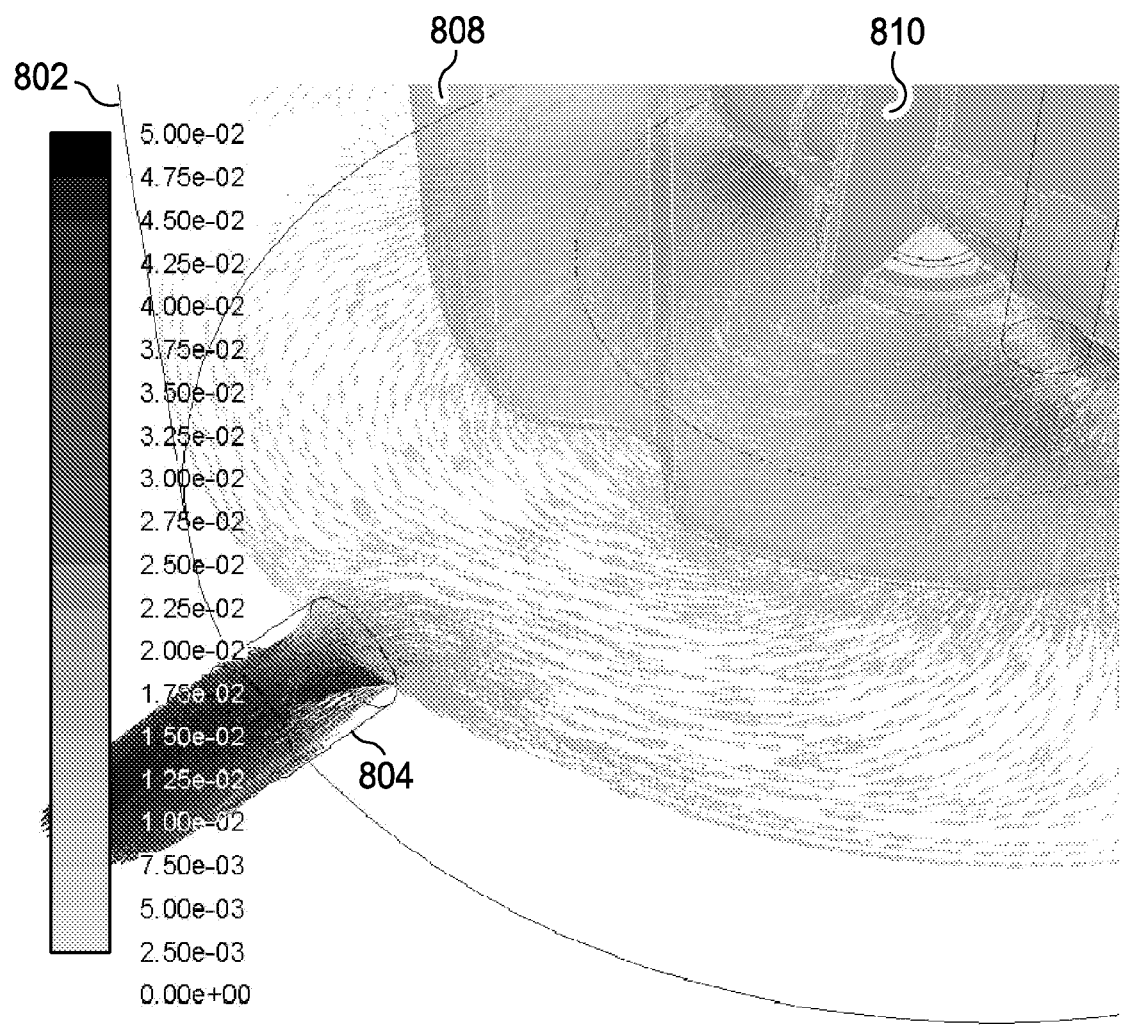

FIGS. 8B, 8C and 8D show the velocity vectors, grey shaded indicate the velocity magnitude at selected horizontal plane (FIGS. 8B and 8D) and the vertical plane (FIG. 8C). As can be seen, the velocity has maximum value in the wake of the mixer 810. It can also be seen that media flows through the inner flask porous membrane wall 808 to the annular space formed by the internal and external walls of the flask (FIG. 8B) and is drawn out of the vessel 802 through the vacuum outlet 804 (FIG. 8C).

Figure 8E:
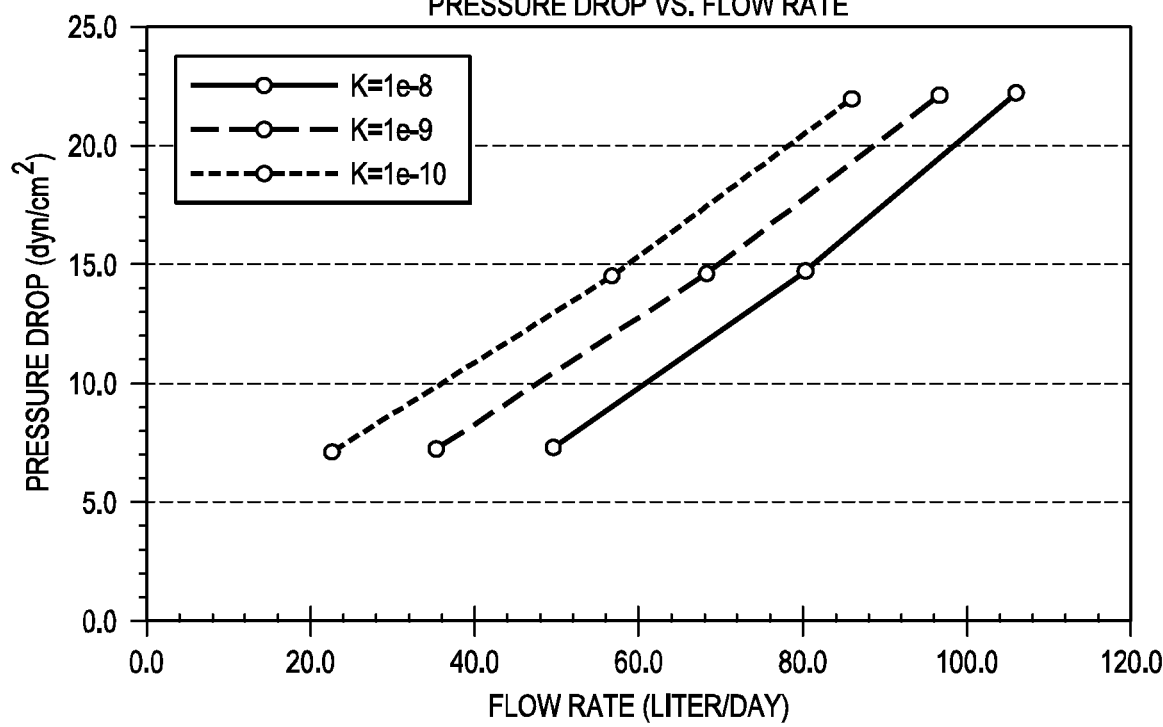
FIG. 8E is a graph illustrating a pressure drop (y axis) versus flow rate (x axis) obtained from the FLUENT model which shows the feasibility of the perfusion bioreactor in accordance with the present disclosure.
Figure 8F:
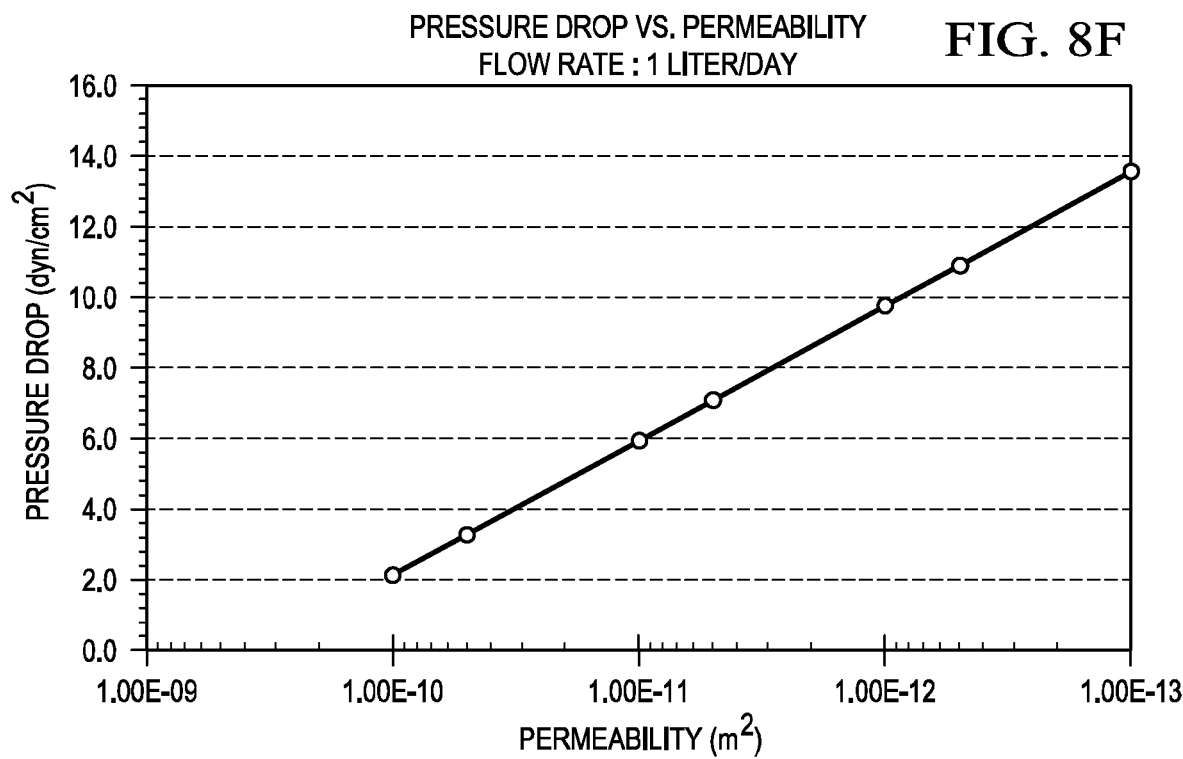
FIG. 8F is a graph illustrating a pressure drop (y axis) versus permeability (x axis) that was extrapolated from the FLUENT model which shows the feasibility of the perfusion bioreactor in accordance with the present disclosure; and, FIG. 9 is a flowchart illustrating the basic steps of a method for using the perfusion bioreactors shown in FIGS. 2-6 to perform a continuous cell culture in accordance with an embodiment of the present disclosure.

The CFD model was used to calculate the pressure drop as a function of flow rate for various values of membrane permeability by running a parametric study with permeability and vacuum pressure as the independent variables and volume flow rate as the dependent variable. The results of this study are shown in FIG. 8E which illustrates a graph of pressure drop (y axis) versus flow rate (x axis). It should be noted that a converged solution for $K<10^{-10}$ m$^2$ was not achieved. Therefore, an extrapolation of the CFD model results was used to calculate the pressure drop when $K<10^{-10}$ m$^2$ at a flow rate of 1 L/day. The extrapolated results are shown in FIG. 8F which illustrates a graph of pressure drop (y axis) versus permeability (x axis).

A comparison of FIG. 7 and FIG. 8E shows that the CFD model predicts higher pressure drop across the porous membrane as compared to the analytical solution. This is reasonable as Darcy's law neglects the inertial term which adds to the pressure drop. For this particular application, the perfusion bioreactor 200, 200' and 200" would likely have a membrane permeability with values in the range between 1 $e^{-10}$ to 1 $e^{-13}$ m$^2$. For this range of membrane permeability, both the analytical and numerical models predicted low pressure drops (<20 dyne/cm$^2$) for the desired flow rate of 1 L/day which proves the feasibility of the design of the perfusion bioreactor 200, 200' and 200" in accordance with the present disclosure.

Figure 9:
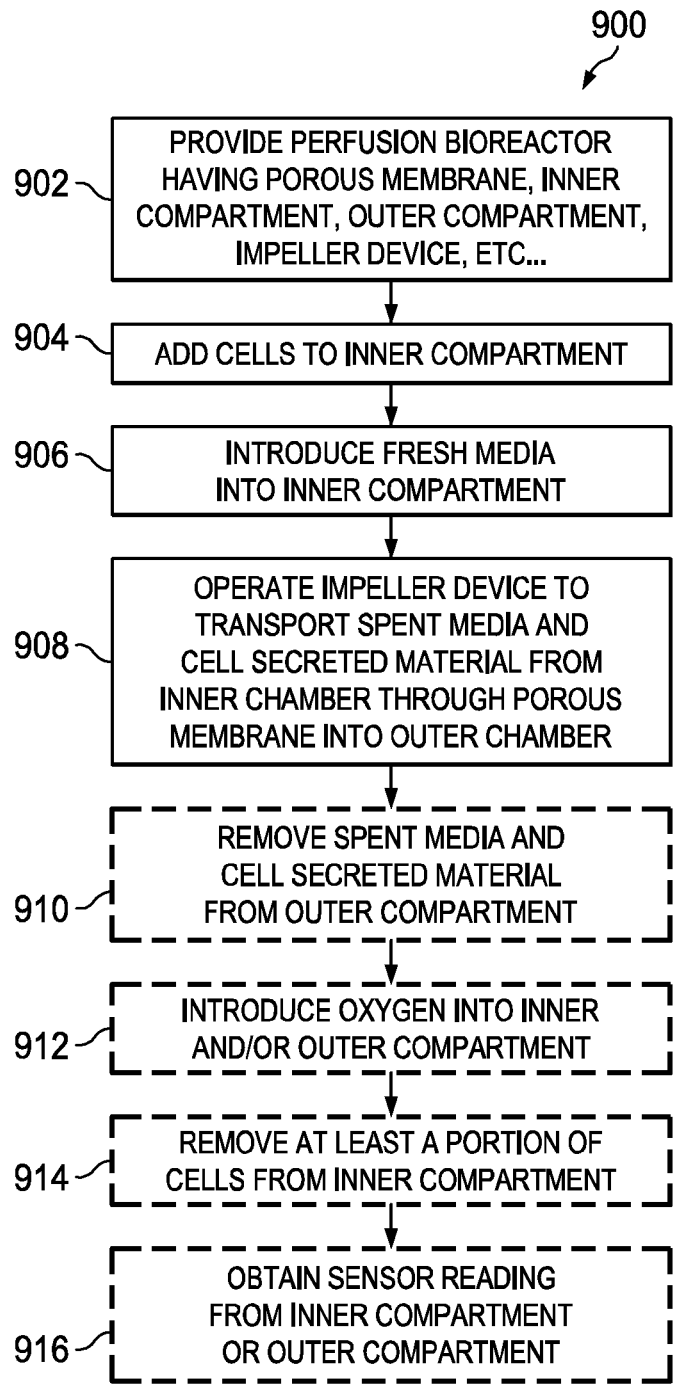

Referring to FIG. 9, there is provided a flowchart illustrating the basic steps of a method 900 for using the perfusion bioreactors 200, 200' and 200" to perform a continuous cell culture in accordance with an embodiment of the present disclosure. Beginning at step 902, the perfusion bioreactor 200, 200' or 200" is provided, wherein the perfusion bioreactor comprises: (i) a vessel 202 having an opening 214 and a cavity 216; (ii) a lid 204 attachable to the vessel 202 to cover the opening 214; (iii) a porous membrane 206 disposed within the cavity 216 to divide the cavity 216 into an inner compartment 218 and an outer compartment 220; (iv) a fresh media port 208 extending through the vessel 202 or the lid 204, where the fresh media port 208 is configured to receive a fresh media tube 224 that has an end located in the inner compartment 218; (v) a spent media port 210 extending through the vessel 202 or the lid 204, where the spent media port 210 is configured to receive a spent media tube 228 that has an end located in the outer compartment 220; (vi) a gas sparger port 236 (optional) extending through the vessel 202 or the lid 204, where the gas sparger port 236 is connected to a gas sparger 244 that has an end located in the inner compartment 218 or the outer compartment 220; (vii) a bleed-off port 238 (optional) extending through the vessel 202 or the lid 204, where the bleed-off port 238 is configured to receive a bleed-off tube 250 that has an end located in the inner compartment 218; (viii) a sensor port 240 (optional) extending through the vessel 202 or the lid 204, where the sensor port 240 is connected to a sensor 254 that has an end located in the inner compartment 218 or the outer compartment 220; and (viiii) an mixer device 212 having an impeller 232 and a shaft 234 which are disposed within the inner compartment 218. At step 904, cells 222 are added to the inner compartment 218. At step 906, fresh media is introduced through the fresh media tube 224 into the inner compartment 218. At step 908, the mixer device 212 is operated to rotate the mixer 232 within the inner compartment 218 to enable transportation of spent media and cell secreted material (e.g., recombinant protein, antibody, virus particles, DNA, RNA, sugars, lipids, biodiesel, inorganic particles, butanol, metaboloic byproducts) through the porous membrane 206 into the outer compartment 220. At step 910 (optional), the spent media and the cell secreted material are removed through the spent media tube 228 from the outer compartment 220. At step 912 (optional), the gas sparger 244 is used to introduce oxygen into the inner compartment 218, or the outer compartment 220, or both compartments 218 and 220. At step 914 (optional), at least a portion of the cells 222 are removed from the inner compartment 218 through the bleed-off tube 250 to control the cell density in the inner compartment 218. At step 916 (optional) a sensor reading is obtained from the sensor 254. For example, the sensor 254 can be: a $DO_2$ sensor, a $CO_2$ sensor, a pH sensor, a cell density sensor, a glucose sensor, a flow or shear stress and temperature sensor.

In view of the foregoing, there is disclosed a perfusion bioreactor which has an inner volume (inner compartment) where cells can be cultivated in a growth medium through agitation provided by an mixer, and an outer volume (outer compartment) separated from the inner volume (inner compartment) through a porous membrane. The porous membrane has small enough pores (e.g., <15 μm for CHO cells—otherwise depends on size of cells) so as to block the cells but allow for the growth medium and cell secreted material (e.g., recombinant protein, antibody, virus particles, DNA, RNA, sugars, lipids, biodiesel, inorganic particles, butanol, metabolic byproducts) to flow from the inner volume (inner compartment) to the outer volume (outer compartment). Fresh media is continuously fed to the inner volume (inner compartment) of the vessel through a feed tube while nutrient-depleted media flows out of the inner volume into the outer volume and out of the vessel through a vacuum port (e.g., spent media tube).

The disclosed perfusion bioreactor effectively integrates a cell retaining membrane within a cell culture vessel so as to allow a continuous cell culture wherein via perfusion the spent media and cell secreted material (e.g., recombinant protein, antibody, virus particles, DNA, RNA, sugars, lipids, biodiesel, inorganic particles, butanol, metabolic byproducts) are passed through the permeable cell retaining membrane. The perfusion bioreactor can be used in bioprocess for either production scale or research scale. The perfusion bioreactor is a marked-improvement over the prior art devices since it does not require mechanical and motional efforts as in the traditional spin filter and ATF techniques to partition the cells from the spent media. The membrane or mesh structure allows the cells to be retained while allowing the media and cell secreted material to flow through the membrane. The inventors have done modeling to validate that this approach is valid (see FIGS. 7-8F). In addition, the inventors have made prototypes of perfusion bioreactors 200' and 200" and have observed them to operate robustly to allow antibodies to pass through the porous membrane while allowing cells to be retained (see FIGS. 5A-6).

In an aspect (1) the disclosure provides for a perfusion bioreactor (200, 200', 200") comprising: a vessel (202) having an at least one opening (214) and a cavity (216); at least one lid (204) attachable to the vessel to cover the at least one opening; a porous membrane (206) disposed within the cavity to divide the cavity into an inner compartment (218) and an outer compartment (220); a fresh media port (208) extending through the vessel or the at least one lid; a spent media port (210) extending through the vessel or the at least one lid; and, an mixer device (212) comprising an impeller (232) and a shaft (234), wherein the impeller and the shaft are disposed within the inner compartment.

In another aspect (2) the disclosure provides the perfusion bioreactor of aspect (1), further comprising a gas sparger port (236) extending through the vessel or the at least one lid.

In another aspect (3) the disclosure provides the perfusion bioreactor of aspect (1 or 2), further comprising a bleed-off port (238) extending through the vessel or the at least one lid.

In another aspect (4) the disclosure provides the perfusion bioreactor of any one of aspects (1-3), further comprising a sensor port (240) extending through the vessel or the at least one lid.

In another aspect (5) the disclosure provides the perfusion bioreactor of any one of aspects (1-4), wherein the vessel or the lid further comprises a vent (242) in communication with the cavity.

In another aspect (6) the disclosure provides the perfusion bioreactor of any one of aspects (1-5), wherein the vessel further comprises a gas permeable housing material (247).

In another aspect (7) the disclosure provides the perfusion bioreactor of any one of aspects (1-6), wherein the porous membrane is attached to an opening (249) within an inner vessel (246), and wherein the inner vessel is disposed within the cavity of the vessel.

In another aspect (8) the disclosure provides the perfusion bioreactor of any one of aspects (1-7), wherein the inner vessel further comprises one or more air exchange windows (221) or a vent in communication with the cavity.

In another aspect (9) the disclosure provides the perfusion bioreactor of any one of aspects (1-8), wherein the porous membrane having pores therein with sizes ranging from about 0.5 to about 150 microns.

In another aspect (10) the disclosure provides the perfusion bioreactor of aspect (1 or 2), wherein the porous membrane further has an inert coating thereon.

In another aspect (11) the disclosure provides the perfusion bioreactor of aspect (2), wherein the impeller is attached to one end of the shaft, and wherein another end of the shaft is rotatably attached to and extends downward from the removable lid.

In another aspect (12) the disclosure provides the perfusion bioreactor of aspect (1), wherein the mixer device further comprises a spin filter (243).

In another aspect (13) the disclosure provides the perfusion bioreactor of aspect (1 or 12), wherein the mixer device further comprises a membrane clearing blade (258) attached to a body of the shaft.

In another aspect (14) the disclosure provides the perfusion bioreactor of aspect (1), wherein the mixer device further comprises a magnetic stir plate (255) located external to the vessel, and wherein the magnetic stir plate is configured to rotate the impeller and the shaft.

In an aspect (15) the disclosure provides for a method (900) for performing a continuous cell culture, the method comprising steps of: (a) providing (902) a perfusion bioreactor (200, 200', 200"), the perfusion bioreactor comprising: (i) a vessel (202) having at least one opening (214) and a cavity (216); (ii) at least one lid (204) attachable to the vessel to cover the opening; (iii) a porous membrane (206) disposed within the cavity to divide the cavity into an inner compartment and an outer compartment; (iv) a fresh media port (208) extending through the vessel or the at least one lid, wherein the fresh media port is configured to receive a fresh media tube (224) that has an end located in the inner compartment; (v) a spent media port (210) extending through the vessel or the at least one lid, wherein the spent media port is configured to receive a spent media tube (228) that has an end located in the outer compartment; and, (vi) an mixer device (212) comprising an impeller (232) and a shaft (234), wherein the impeller and shaft are disposed within the inner compartment; (b) adding (904) cells (222) to the inner compartment; (c) introducing (906) fresh media through the fresh media tube into the inner compartment; (d) operating (910) the mixer device to rotate the mixer within the inner compartment to enable transportation of spent media and cell secreted material through the porous membrane into the outer compartment; and (e) removing (912) the spent media and the cell secreted material through the spent media tube from the outer compartment.

In another aspect (16) the disclosure provides the method of aspect (15), further comprising: a gas sparger port (236) extending through the vessel or the at least one lid, wherein the gas sparger port is connected to a gas sparger (244), and wherein the gas sparger has an end located in at least one of the inner compartment and the outer compartment; and, the method further comprises using (914) the gas sparger to introduce oxygen into the outer compartment.

In another aspect (17) the disclosure provides the method of aspect (15), further comprising: a bleed-off port (238) extending through the vessel or the at least one lid, wherein the bleed-off port is configured to receive a bleed-off tube (250), and wherein the bleed-off tube has an end located in the inner compartment; and, the method further comprises removing (916) at least a portion of the cells from the inner compartment through the bleed-off tube.

In another aspect (18) the disclosure provides the method of aspect (15), further comprising a sensor port (240) extending through the vessel or the at least one lid, wherein the sensor port is connected to a sensor (254), and wherein the sensor has an end located in the inner compartment or the outer compartment; and, the method further comprises obtaining (918) a sensor reading from the sensor.

In another aspect (19) the disclosure provides the method of aspect (15), wherein the porous membrane is attached to an opening (249) within an inner vessel (246), wherein the inner vessel is disposed within the cavity of the vessel.

In another aspect (20) the disclosure a perfusion bioreactor of any one of aspects 1-7, wherein the vessel or the at least one lid further comprises a vent in communication with the cavity.

In another aspect (21) the disclosure provides a perfusion reactor of any one of aspects 1-8 wherein the vessel further comprises a gas permeable housing material.

In another aspect (22) the disclosure provides a perfusion bioreactor of any one of aspects 1-9, wherein the porous membrane is attached to an opening within an inner vessel, and wherein the inner vessel is disposed within the cavity of the vessel.

It will be appreciated that the various disclosed embodiments may involve particular features, elements or steps that are described in connection with that particular embodiment. It will also be appreciated that a particular feature, element or step, although described in relation to one particular embodiment, may be interchanged or combined with alternate embodiments in various non-illustrated combinations or permutations.

It is also to be understood that, as used herein the terms "the," "a," or "an," mean "at least one," and should not be limited to "only one" unless explicitly indicated to the contrary. Thus, for example, reference to "an opening" includes examples having two or more such "openings" unless the context clearly indicates otherwise.

Ranges can be expressed herein as from "about" one particular value, and/or to "about" another particular value. When such a range is expressed, examples include from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

All numerical values expressed herein are to be interpreted as including "about," whether or not so stated, unless expressly indicated otherwise. It is further understood, however, that each numerical value recited is precisely contemplated as well, regardless of whether it is expressed as "about" that value. Thus, "a dimension less than 10 mm" and "a dimension less than about 10 mm" both include embodiments of "a dimension less than about 10 mm" as well as "a dimension less than 10 mm."

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to a method comprising A+B+C include embodiments where a method consists of A+B+C, and embodiments where a method consists essentially of A+B+C.

Although multiple embodiments of the present disclosure have been illustrated in the accompanying Drawings and described in the foregoing Detailed Description, it should be understood that the disclosure is not limited to the disclosed embodiments, but is capable of numerous rearrangements, modifications and substitutions without departing from the disclosure as set forth and defined by the following claims.

The invention claimed is:

1. A perfusion bioreactor comprising:
an outer vessel having a housing comprised at least in part of gas permeable membrane, at least one opening and a cavity;
an inner vessel disposed within the cavity of the outer vessel;
at least one lid attachable to the outer vessel to cover the at least one opening;
a porous membrane disposed within the cavity to divide the cavity into an inner compartment and an outer compartment disposed radially outward from and surrounding the inner compartment, the porous membrane defining an outer circumferential surface of the inner compartment;
a fresh media port extending through the outer vessel or the at least one lid and configured to receive a fresh media tube that has an end located in the inner compartment;
a spent media port extending through the outer vessel or the at least one lid and configured to receive a spent media tube that has an end located in the outer compartment; and,
a mixer disposed within the inner compartment,
wherein the porous membrane is attached to an opening within the inner vessel.

2. The perfusion bioreactor of claim 1 wherein the mixer comprises an impeller and a shaft, wherein the impeller and the shaft are disposed within the inner compartment.

3. The perfusion bioreactor of claim 1 wherein the lid is removably attached to the outer vessel.

4. The perfusion bioreactor of claim 1 wherein the outer vessel or the porous membrane or both are flexible.

5. The perfusion bioreactor of claim 1, further comprising a gas sparger port extending through the outer vessel or the at least one lid.

6. The perfusion bioreactor of claim 1, further comprising a bleed-off port extending through the outer vessel or the at least one lid.

7. The perfusion bioreactor of claim 1, further comprising a sensor port extending through the outer vessel or the at least one lid.

8. The perfusion bioreactor of claim 1, wherein the outer vessel or the at least one lid further comprises a vent in communication with the cavity.

9. The perfusion bioreactor of claim 1, wherein the inner vessel further comprises one or more air exchange windows.

10. The perfusion bioreactor of claim 1, wherein the porous membrane having pores therein with sizes ranging from about 0.5 to about 150 microns.

11. The perfusion bioreactor of claim 1, wherein the porous membrane further has an inert coating thereon.

12. The perfusion bioreactor of claim 2, wherein the impeller is attached to one end of the shaft, and wherein another end of the shaft is rotatably attached to and extends downward from the at least one lid.

13. The perfusion bioreactor of claim 1, wherein the mixer device further comprises a membrane clearing blade attached to a body of the shaft and configured to brush the porous membrane.

14. The perfusion bioreactor of claim 1, wherein the mixer device further comprises a magnetic stir plate located external to the outer vessel, and wherein the magnetic stir plate is configured to rotate the mixer.

15. A method for performing a continuous cell culture, the method comprising steps of:
   providing a perfusion bioreactor, the perfusion bioreactor comprising:
      an outer vessel having at least one opening and a cavity;
      an inner vessel disposed within the cavity of the outer vessel;
      at least one lid attachable to the outer vessel to cover the at least one opening;
      a porous membrane disposed within the cavity to divide the cavity into an inner compartment and an outer compartment disposed radially outward from and surrounding the inner compartment, wherein the porous membrane is attached to an opening within the inner vessel;
      a fresh media port extending through the outer vessel or the at least one lid, wherein the fresh media port is configured to receive a fresh media tube that has an end located in the inner compartment;
      a spent media port extending through the outer vessel or the at least one lid, wherein the spent media port is configured to receive a spent media tube that has an end located in the outer compartment; and,
      a mixer disposed within the inner compartment;
   adding cells to the inner compartment;
   introducing fresh media through the fresh media tube into the inner compartment;
   operating the mixer device to rotate the mixer within the inner compartment to enable transportation of spent media and cell secreted material through the porous membrane into the outer compartment; and
   removing the spent media and the cell secreted material through the spent media tube from the outer compartment.

16. The method of claim 15, further comprising:
   a gas sparger port extending through the outer vessel or the at least one lid, wherein the gas sparger port is connected to a gas sparger, and wherein the gas sparger has an end located in at least one of the inner compartment and the outer compartment; and,
   the method further comprises using the gas sparger to introduce oxygen into the outer compartment or inner compartment or both.

17. The method of claim 15, further comprising:
   a bleed-off port extending through the outer vessel or the at least one lid, wherein the bleed-off port is configured to receive a bleed-off tube, and wherein the bleed-off tube has an end located in the inner compartment; and,
   the method further comprises removing at least a portion of the cells from the inner compartment through the bleed-off tube.

18. The method of claim 15, further comprising:
   a sensor port extending through the outer vessel or the at least one lid, wherein the sensor port is connected to a sensor, and wherein the sensor has an end located in the inner compartment or the outer compartment; and,
   the method further comprises obtaining a sensor reading from the sensor.

\* \* \* \* \*